United States Patent [19]

Höltke et al.

[11] Patent Number: 5,344,757

[45] Date of Patent: * Sep. 6, 1994

[54] PROCESS FOR THE DETECTION OF NUCLEIC ACIDS

[75] Inventors: Hans-Joachim Höltke, Tutzing; Rudolf Seibl, Penzberg; Gudrun Schmitz, Bernried; Hans R. Schöler, Göttingen; Christoph Kessler, München; Ralf Mattes, Stuttgart, all of Fed. Rep. of Germany

[73] Assignee: Boehringer Mannheim GmbH, Mannheim-Waldhof, Fed. Rep. of Germany

[ * ] Notice: The portion of the term of this patent subsequent to Mar. 30, 2010 has been disclaimed.

[21] Appl. No.: 415,307

[22] PCT Filed: Jan. 12, 1989

[86] PCT No.: PCT/EP89/00026

§ 371 Date: Jan. 9, 1990

§ 102(e) Date: Jan. 9, 1990

[87] PCT Pub. No.: WO89/06698

PCT Pub. Date: Jul. 27, 1989

[30] Foreign Application Priority Data

Jan. 12, 1988 [DE] Fed. Rep. of Germany ....... 3800642
Apr. 20, 1988 [DE] Fed. Rep. of Germany ....... 3813278

[51] Int. Cl.$^5$ .............................................. C12Q 1/68
[52] U.S. Cl. ...................................... 435/6; 536/24.3; 536/25.32
[58] Field of Search ................. 435/6, 7.1, 7.92; 536/24.3, 24.31, 24.32, 25.32

[56] References Cited

U.S. PATENT DOCUMENTS 5,198,537  3/1993  Huber et al. ...................... 530/406

FOREIGN PATENT DOCUMENTS 0173251  3/1986  European Pat. Off. ..... C07H 21/00

OTHER PUBLICATIONS

Langer et al. (Nov. 1981), Proc. Natl. Acad. Sci. USA 78(11):6633–6637.
Hunter et al. (Sep. 1982), J. Immunol. 129(3):1165–1172.
Lewis et al. (1987), J. Clin. Pathol. 40:163–166.
Forster et al. (1985), Nucl. Acids. Res. 13(3):745–761.
Saiki et al. (1985), Science 230:1350–1354.

*Primary Examiner*—Richard A. Schwartz
*Assistant Examiner*—Philip Carter
*Attorney, Agent, or Firm*—Felfe & Lynch

[57] ABSTRACT

For the detection of nucleic acids of definite sequence by hybridisation with a complementary nucleic acid probe which contains bound via a chemical bonding at least one hapten as labelling one uses, as hapten, a steroid which is bound via a bridge of at least 4 atoms length to at least one position of the nucleic acid probe which does not participate in hydrogen bridge formation and detects the hybridised probe via an in turn labelled anti-hapten antibody.

35 Claims, 11 Drawing Sheets

Dig-11(16)-dUTP

Photodigoxigenin

FIG. 4
Highly sensitive DNA-detection linear denatured DNA

+random Hexanucleotide      +dATP, dCTP, dGTP, dTTP
       +Klenow              +Dig-11-dUTP Incubation 37C
DNA Synthesis/Labelling Filter-bound DNA + Labelled denatured DNA = Hybrid + Antibody conjugate
<Dig> AP bound Antibody Colour reaction red/blue colour Synthesis scheme for Digoxigenin-3-hemisuccinate/
N'-(4-azidobenzoyl)/-8-amino-3,6-dioxaoctylamide(Photodigoxigenin)

I          II          III

III

IV

V

Comparison of the Sensitivities of Digoxigenin and Biotin

FIG. 9
Comparison of the sensitivities of an enzymatic labelling according to the invention (A) with a known chemical labelling (B)
FIG.9A
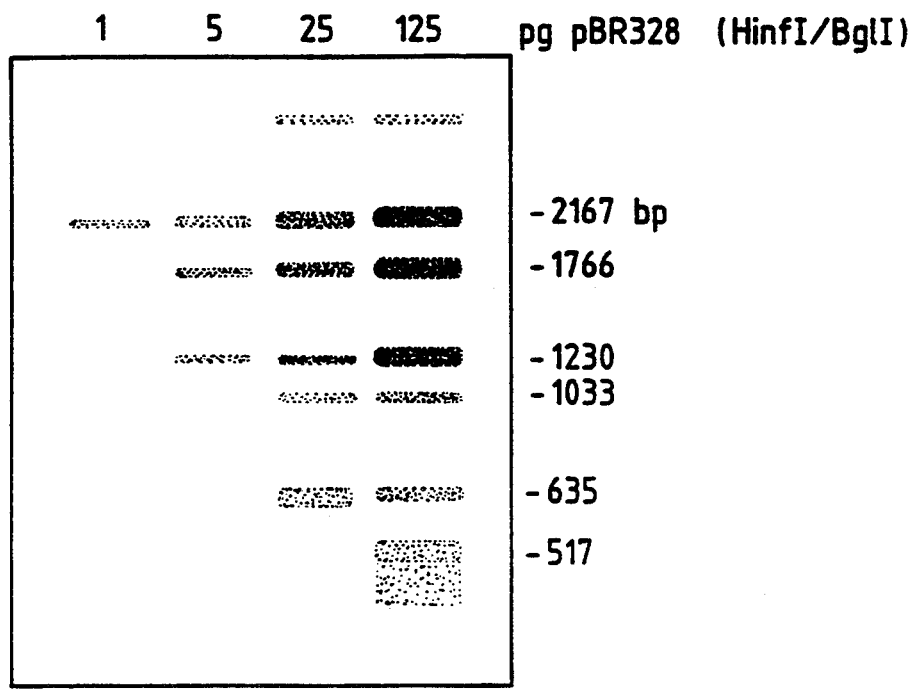
FIG.9B
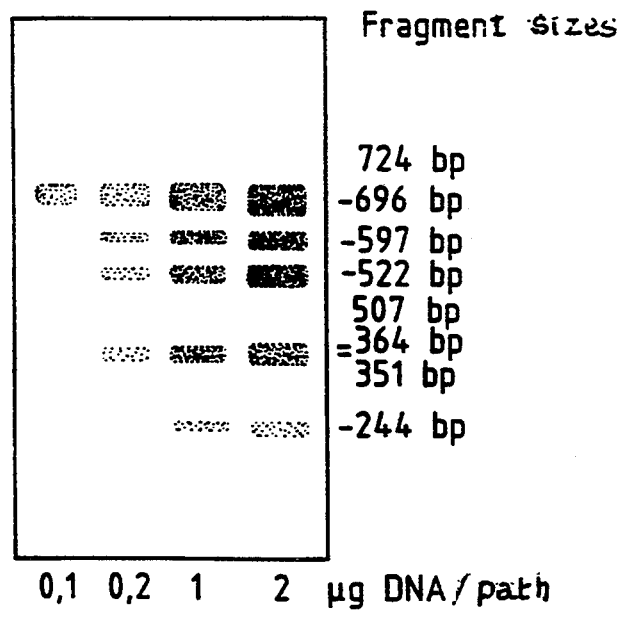

FIG. 10A

```
   1 GAATACAAGC TTGCATGCCT GCAGGTCGAC TCTAGAGGAT CCCCGGGTAC
  51 CGAGCTCGAA TTCCGGTCTC CCTATAGTGA GTCGTATTAA TTTCGATAAG
 101 CCAGCTGGGC CTCGCGCGTT TCGGTGATGA CGGTGAAAAC CTCTGACACA
 151 TGCAGCTCCC GGAGACGGTC ACAGCTTGTC TGTAAGCGGA TGCCGGGAGC
 201 AGACAAGCCC GTCAGGGCGC GTCAGCGGGT GTTGGCGGGT GTCGGGGCGC
 251 AGCCATGACC CAGTCACGTA GCGATAGCGG AGTGTATATA CTGGCTTAAC
 301 TATGCGGCAT CAGAGCAGAT TGTACTGAGA GTGCACCATA TGCGGTGTGA
 351 AATACCGCAC AGATGCGTAA GGAGAAAATA CCGCATCAGG CGCTCTTCCG
 401 CTTCCTCGCT CACTGACTCG CTGCGCTCGG TCGTTCGGCT GCGGCGAGCG
 451 GTATCAGCTC ACTCAAAGGC GGTAATACGG TTATCCACAG AATCAGGGGA
 501 TAACGCAGGA AAGAACATGT GAGCAAAAGG CCAGCAAAAG GCCAGGAACC
 551 GTAAAAAGGC CGCGTTGCTG GCGTTTTTCC ATAGGCTCCG CCCCCCTGAC
 601 GAGCATCACA AAAATCGACG CTCAAGTCAG AGGTGGCGAA ACCCGACAGG
 651 ACTATAAAGA TACCAGGCGT TTCCCCCTGG AAGCTCCCTC GTGCGCTCTC
 701 CTGTTCCGAC CCTGCCGCTT ACCGGATACC TGTCCGCCTT TCTCCCTTCG
 751 GGAAGCGTGG CGCTTTCTCA ATGCTCACGC TGTAGGTATC TCAGTTCGGT
 801 GTAGGTCGTT CGCTCCAAGC TGGGCTGTGT GCACGAACCC CCCGTTCAGC
 851 CCGACCGCTG CGCCTTATCC GGTAACTATC GTCTTGAGTC AACCCGGTA
 901 AGACACGACT TATCGCCACT GGCAGCAGCC ACTGGTAACA GGATTAGCAG
 951 AGCGAGGTAT GTAGGCGGTG CTACAGAGTT CTTGAAGTGG TGGCCTAACT
1001 ACGGCTACAC TAGAAGGACA GTATTTGGTA TCTGCGCTCT GCTGAAGCCA
```

FIG. 10B

```
1051  GTTACCTTCG GAAAAAGAGT TGGTAGCTCT TGATCCGGCA AACAAACCAC
1101  CGCTGGTAGC GGTGGTTTTT TTGTTTGCAA GCAGCAGATT ACGCGCAGAA
1151  AAAAAGGATC TCAAGAAGAT CCTTTGATCT TTTCTACGGG GTCTGACGCT
1201  CAGTGGAACG AAAACTCACG TTAAGGGATT TTGGTCATGA GATTATCAAA
1251  AAGGATCTTC ACCTAGATCC TTTTAAATTA AAAATGAAGT TTTAAATCAA
1301  TCTAAAGTAT ATATGAGTAA ACTTGGTCTG ACAGTTACCA ATGCTTAATC
1351  AGTGAGGCAC CTATCTCAGC GATCTGTCTA TTTCGTTCAT CCATAGTTGC
1401  CTGACTCCCC GTCGTGTAGA TAACTACGAT ACGGGAGGGC TTACCATCTG
1451  GCCCCAGTGC TGCAATGATA CCGCGAGACC CACGCTCACC GGCTCCAGAT
1501  TTATCAGCAA TAAACCAGCC AGCCGGAAGG GCCGAGCGCA GAAGTGGTCC
1551  TGCAACTTTA TCCGCCTCCA TCCAGTCTAT TAATTGTTGC CGGGAAGCTA
1601  GAGTAAGTAG TTCGCCAGTT AATAGTTTGC GCAACGTTGT TGCCATTGCT
1651  ACAGGCATCG TGGTGTCACG CTCGTCGTTT GGTATGGCTT CATTCAGCTC
1701  CGGTTCCCAA CGATCAAGGC GAGTTACATG ATCCCCCATG TTGTGCAAAA
1751  AAGCGGTTAG CTCCTTCGGT CCTCCGATCG TTGTCAGAAG TAAGTTGGCC
1801  GCAGTGTTAT CACTCATGGT TATGGCAGCA CTGCATAATT CTCTTACTGT
1851  CATGCCATCC GTAAGATGCT TTTCTGTGAC TGGTGAGTAC TCAACCAAGT
1901  CATTCTGAGA ATAGTGTATG CGGCGACCGA GTTGCTCTTG CCCGGCGTCA
1951  ATACGGGATA ATACCGCGCC ACATAGCAGA ACTTTAAAAG TGCTCATCAT
2001  TGGAAAACGT TCTTCGGGGC GAAAACTCTC AAGGATCTTA CCGCTGTTGA
2051  GATCCAGTTC GATGTAACCC ACTCGTGCAC CCAACTGATC TTCAGCATCT
```

FIG. 10C

```
2101  TTTACTTTCA CCAGCGTTTC TGGGTGAGCA AAAACAGGAA GGCAAAATGC
2151  CGCAAAAAAG GGAATAAGGG CGACACGGAA ATGTTGAATA CTCATACTCT
2201  TCCTTTTTCA ATATTATTGA AGCATTTATC AGGGTTATTG TCTCATGAGC
2251  GGATACATAT TTGAATGTAT TTAGAAAAAT AAACAAATAG GGGTTCCGCG
2301  CACATTTCCC CGAAAAGTGC CACCTGACGT CTAAGAAACC ATTATTATCA
2351  TGACATTAAC CTATAAAAAT AGGCGTATCA CGAGGCCCTT TCGTCTCGCG
2401  CGTTTCGGTG ATGACGGTGA AAACCTCTGA CACATGCAGC TCCCGGAGAC
2451  GGTCACAGCT TGTCTGTAAG CGGATGCCGG GAGCAGACAA GCCCGTCAGG
2501  GCGCGTCAGC GGGTGTTGGC GGGTGTCGGG GCTGGCTTAA CTATGCGGCA
2551  TCAGAGCAGA TTGTACTGAG AGTGCACCAT ATCGACGCTC TCCCTTATGC
2601  GACTCCTGCA TTAGGAAGCA GCCCAGTAGT AGGTTGAGGC CGTTGAGCAC
2651  CGCCGCCGCA AGGAATGGTG CATGCAAGGA GATGGCGCCC AACAGTCCCC
2701  CGGCCACGGG CCTGCCACCA TACCCACGCC GAAACAAGCG CTCATGAGCC
2751  CGAAGTGGCG AGCCCGATCT TCCCCATCGG TGATGTCGGC GATATAGGCG
2801  CCAGCAACCG CACCTGTGGC GCCGGTGATG CCGGCCACGA TGCGTCCGGC
2851  GTAGAGGATC TGGCTAGCGA TGACCCTGCT GATTGGTTCG CTGACCATTT
2901  CCGGGTGCGG GACGGCGTTA CCAGAAACTC AGAAGGTTCG TCCAACCAAA
2951  CCGACTCTGA CGGCAGTTTA CGAGAGAGAT GATAGGGTCT GCTTCAGTAA
3001  GCCAGATGCT ACACAATTAG CTTGTACAT ATTGTCGTTA GAACGCGGCT
3051  ACAATTAATA CATAACCTTS TGTATCATAC ACATACGATT TAGGTGACAC
3101  TATA
```

FIG. 11

| Enzyme | Number of the cleavage positions | Position of the cleavage positions | | | | |
|---|---|---|---|---|---|---|
| Ava II    | 2 | 1546 | 1768 | | | |
| Bgl I     | 2 |  106 | 1528 | | | |
| Eco 31I   | 2 |   71 | 1469 | | | |
| Fin I     | 2 | 2699 | 2908 | | | |
| Hgi EII   | 2 |  335 | 1096 | | | |
| Sph I     | 2 |   17 | 2674 | | | |
| Apy I     | 3 |  543 |  664 |  677 | | |
| Ban II    | 3 |   56 | 2750 | 2764 | | |
| Bbe I     | 3 | 2688 | 2801 | 2822 | | |
| Cfr 10I   | 3 | 1488 | 2821 | 2830 | | |
| Dra I     | 3 | 1274 | 1293 | 1985 | | |
| Eae I     | 3 | 1796 | 2702 | 2832 | | |
| Eco 57I   | 3 | 1063 | 2075 | 2977 | | |
| Eco RII   | 3 |  541 |  662 |  675 | | |
| Gdi II    | 3 | 1796 | 2701 | 2832 | | |
| Hae I     | 3 |  528 |  539 |  991 | | |
| Mme I     | 3 |  730 |  914 | 2966 | | |
| Nar I     | 3 | 2685 | 2798 | 2819 | | |
| Tth 111II | 3 | 1105 | 1112 | 1144 | | |
| Apa LI    | 4 |  331 |  829 | 2075 | 2572 | |
| Bsp HI    | 4 | 1235 | 2243 | 2348 | 2742 | |
| Aha II    | 5 | 1945 | 2327 | 2685 | 2798 | 2819 |
| Ban I     | 5 |   46 | 1356 | 2684 | 2797 | 2818 |
| Fok I     | 5 |  201 | 1374 | 1555 | 1842 | 2485 |
| Mae I     | 5 |   32 | 1010 | 1263 | 1598 | 2864 |
| Mae II    | 5 |  266 | 1218 | 1634 | 2007 | 2327 |
| Nsp I     | 5 |   17 |  152 |  519 | 2436 | 2674 |
| Rsa I     | 5 |   48 |  323 | 1888 | 2564 | 3026 |
| Sec I     | 5 |   41 |   42 |  675 | 2698 | 2704 |

Enzymes which do not cleave

| | | | | |
|---|---|---|---|---|
| Afl II   | Apa I    | Asu II  | Avr II  | Bal I    |
| Bbv II   | Bcl I    | Bgl II  | Bsm I   | Bsp MII  |
| Bss HII  | Bst EII  | Bst XI  | Cla I   | Dra III  |
| Eco RV   | Eco R124 | Esp I   | Hpa I   | Mlu I    |
| Nco I    | Not I    | Nru I   | Nsi I   | Pfi MI   |
| Pma CI   | Ppu MI   | Rsr II  | Sac II  | Sau I    |
| Sfi I    | Sna I    | Sna BI  | Spe I   | Spl I    |
| Stu I    | Sty I    | Xho I   | Xma III | |

PROCESS FOR THE DETECTION OF NUCLEIC ACIDS

The invention concerns a process for the detection of nucleic acids of defined sequence by hybridization with complementary, labelled nucleic acid probe.

One of the most used molecular-biological techniques is the DNA/DNA, RNA/RNA or RNA/DNA hybridization for the detection of homologous nucleic acid sequences. A nucleic acid (DNA or RNA) probe is labelled and brought into contact with a nucleic acid (DNA or RNA) to be investigated, usually fixed on a filter, under hybridization conditions. If there is homology between the nucleic acids used as probe and the nucleic acid to be detected, these forms a hybrid double strand. The hybrids are subsequently detected. Hitherto, the labelling of the probe generally took place by incorporation of radioactively derivatized desoxyribonucleoside triphosphates therein. The detection of the hybrids then took place by autoradiography. Such conventional, radioactively-labelled DNA probes are very effective and sensitive but problems arise due to the need to handle radioactive material. Handling with radioactive material requires specially trained personnel since handling by unskilled individuals, leads to endangering of the laboratory safety. Furthermore, the disposal of radioactive materials is a further problem. In addition, the radioactively-labelled samples, because of the half-life times of the radioactive materials used, can only be used for a certain period of time after their preparation. When the detection of small amounts of DNA are to be detected, the necessary time of exposure of the autoradiography can also be very long, on line of days to weeks.

Besides the radioactively-labelled systems for the detection of nucleic acids, non-radioactive methods are known, whereby the nucleic acid samples used are modified with biotin molecules (U.S. Pat. No. 4,687,732, EP-A 0063879), digoxin-/$T_3$-/$T_4$ molecules (EP-A-0173251) or with alkyl-/butyl-/ethyl-/sulphonic acid-/nitroso molecules (EP-A 128018). The incorporation of these low molecular weight molecules into the complementary nucleic acid probe thereby takes place chemically, photochemically or enzymatically. They are then hybridized with the nucleic acid sequence to be detected. The detection of the hybrids then takes place via binding of the low molecular weight molecule by a (strept)avidin-labelling enzyme conjugate in the case of biotin, antidigoxin/-$T_3$-/-$T_4$-antibody-labelling enzyme conjugate in the the case of digoxin-/$T_3$-/$T_4$-molecules or via anti-alkyl-/-butyl-/-ethyl-/-sulphonic acid-/-nitroso-antibody-labelling enzyme conjugates. The detection of the hybridization product takes place by the determination of the enzymatic activity of the labelling enzyme, using coupled coloured materials systems. However, in the case of the method of EP-A-0 173 251, the binding of the digoxin-/$T_3$-/$T_4$ molecules takes place on an N-atom participating in the hydrogen bridge formation of one or more bases of the nucleic acid probe.

In these cases, hybridization is impaired, especially when the probe has been multiply modified. With the exception of the biotin/(strept)avidin system, the sensitivity of the known non-radioactive systems as compared to radioactive systems, is at least 10 to 100 times lower. The uniquely high sensitivity of the non-radioactive detection of biotin/(strept)avidin system is to be attributed to the high binding constant ($K=10^{15}$ mol$^{-1}$) See, e.g. Kinow; Proc. Natl. Acad. Sci. USA 80 (1983) 4045). The maximum achievable sensitivity of the biotin/(strept)avidin system lies, as also in the case of radioactive labelling, in the detection of from 0.1 pg. to 1 pg. DNA in the dot-blot assays and in detection of "single-copy" genes, i.e. of genes which occur only once the genome, in using from 1 to 10 μg. of genomic DNA fragments in genomic blots. However, the utilization of the biotin/(strept)avidin system has a decisive disadvantage in that it is very subject to disturbance since the vitamin biotin occurs in almost all biological materials (Biochem. Biophys. Acta 29 (1985) 225; Biochem. Biophys. Acta 41 (1960) 122).

Therefore, it is an object of the invention to make available a process for the detection of nucleic acids which permits the use of a non-radioactive label and is less subject to disturbance than the biotin/(strept)avidin system but, on the other hand, achieves high detection sensitivity equivalent to that obtained using radioactive or biotin/(Strept)avidin labels.

According to the invention, this is achieved by hybridization with a complementary nucleic acid probe which, via a chemical bond, contains bound at least one hapten as label which is a steroid bound to at least one position of the nucleic acid which does not participate in hydrogen bond formation via a bridge of at least 4 atoms length, followed by detection of the hybridized probe using labelled anti-hapten antibody.

As steroid, digoxigenin or digoxin are preferred.

The process according to the invention makes possible the detection of 0.5 pg. to 0.05 pg. homologous DNA in the dot-blot and of "single copy" genes in 5 μg. to 0.5 μg. genomic DNA fragments. In both types of detection, the detection sensitivity is at least analogous to the detection sensitivity of the biotin/(strept)avidin system. This is surprising since the binding constant of the biotin/(strept)avidin system ($K=10^{15}$ mol$^{-1}$, Green N. M. (1975) Adv. Protein Chem. 29, 85-133; Chaiet, L., Wolf, F. J. (1964) Arch. Biochem. Biophys. 106, 1-5) is higher by at least a factor of $10^5$ than that of digoxigenin or digoxin/with the corresponding antibody systems ($K=2\times10^8$ mol$^{-1}$ -$7\times10^9$ mol$^{-1}$, Hunter et al., J. immunol. Vol. 129, No. 3 (1982) 1165) and, in addition, the biotin/(strept)avidin exchange action is favored by the presence of 4 biotin binding positions on (strept)avidin.

A further surprising technical advantage is that in the case of the use of digoxigenin or digoxin and the antibodies belonging thereto, very much less non-specific binding (background) results in the filter on which the nucleic acid to be detected is fixed than in the case of use of biotin/(strept)avidin.

The carrying out of the process according to the invention for the detection of nucleic acids can be divided up into three steps.

1. The derivatization of the nucleic acid sample serving as detection reagent with the hapten.
2. the hybridization and
3. the detection of the hybrids.

For the derivatization of nucleic acids (DNA and RNA), various methods can be employed (Molecular Cloning, Maniatis et al., (1982) Cold Spring Harbor Laboratory, Cold Spring Harbor, N.Y. The incorporation of the hapten can hereby take place enzymatically, chemically or photochemically.

In the "random-primed" method (Anal. Biochem. 132 (1983) 6), double-stranded deoxyribonucleic acid probes are first denatured, i.e. the two strands are separated by heating and thereby converted into nucleic acid single strands. In the case of single-stranded desoxyribonucleic acid probes, the denaturing is omitted. Random primers are bound to the deoxyribonucleic acid single strands. These are oligodesoxyribonucleotides of any desired length with differing sequences which hybridize to the complementary sections of the single strand DNA. Subsequently, starting from the 3'-OH ends of the "random primers", the strand complementary to the single strand is synthesised by the action of the enzyme Klenow polymerase or other DNA polymerases (e.g. coded for by T4 or T7 or from *Thermus aquaticus*). The four deoxyribonucleoside triphosphates used as substrate are thereby incorporated. Up to four of these triphosphate types are partly or wholly derivatized by coupling of a steroid via a bridge so that, in the case of the desoxyribonucleic acid synthesis, this steroid is also incorporated. A preferred steroid-derivatized nucleoside triphosphate is illustrated in FIG. 1 with two different preferred bridge chain lengths.

The specific primer method involves the use of short chain oligodeoxyribonucleotides which, for the most part, have different sequences rather than random primers. The short chain deoxyribonucleotides used have specific sequences. These specific primers bind uniformly only to the complementary sequence section of the single strand DNA. In contradistinction to the "random primer" method, the synthesis of the complementary strand is only started from this particular sequence section. The four deoxyribinucleoside triphosphate types offered as substrate are incorporated therein. Up to four of these triphosphate types are derivatized partly or wholly by coupling of a steroid via a bridge, so that, in the case of the deoxyribonucleic acid synthesis, this steroid is incorporated therein.

In the case of the "reversed transcriptions" method (Efstratiadis, A. F. C., Villa-Komaroff, L. (1979) Genetic Engineering (Stelow, J. K. and Hollaender, A., eds.) Plenum Press, New York and London, Vol. 1. pp. 1), single-stranded ribonucleic acid probes or double-stranded ribonucleic acid probes are, after denaturing, i.e. conversion into single strands, retrotranscribed, i.e. the corresponding deoxyribonucleic acid formed. For this purpose, oligodeoxyribonucleotides, i.e., the "primers", are bound to the complementary sequence section of the single stranded ribonucleic acid probes. Subsequently, starting from the 3'-OH end of the bound "primer", by action of the enzyme reverse transcriptase, the DNA strand complementary to the RNA single strand is synthesized. Reverse transcriptases of virus AMV or Mo-MLV are preferred. In case of the DNA strand synthesis, the four deoxyribonucleoside triphosphate types used as substrate are incorporated. Up to four of these triphosphate types are partly or wholly derivatized by coupling of a steroid via a bridge into the strand when the DNA is synthesized, this steroid is also incorporated.

In the "fill-in" method, double-stranded desoxyribonucleic acid probes are derivatised with 5'-overhanging single strand ends. For this purpose, with the enzyme Klenow polymerase or other DNA polymerases (e.g. those coded for by phage T4- or T7), the 3'-OH ends of the non-overhanging single strand are elongated complementary to the 5'-overhanging single strand sequence. Depending upon the sequence of the 5'-overhanging single strand region, up to four of the deoxyribonucleoside triphosphate types are thereby incorporated. Up to four of these triphosphate types are, in turn, partly or wholly derivatized by coupling of a steroid via a bridge, so that incorporation of the this steroid is also incorporated into the sequence when the nucleotide to which it is bound is incorporated.

In the "nick-translation" method (J. Mol. Biol. 113 (1977) 237), double-stranded deoxyribonucleic acid probes are incubated simultaneously with the enzyme *E. coli* DNA polymerase I, as well as a small amount of the enzyme DNase I in the presence of the four deoxyribonucleoside triphosphates serving as substrate. By means of the enzyme DNase I, single strand breaks, the so-called "nicks", are produced. 5'- and 3'-ends thereby arise within the broken individual strand. By means of the enzyme *E. coli* DNA polymerase I, the 5'-end-positioned deoxyribonucleosides on the internal single strand breaks are removed simultaneously with the incorporation of a deoxyribonucleotide type on a neighbouring free 3'-OH end. Repetition of the simultaneous breaking and new incorporation of a nucleotide causes the single strand break to migrate in the direction of the 3'-end. Up to four of the triphosphate types serving as substrate are again partly or wholly derivatized by coupling of a steroid via a bridge so that this steroid is incorporated into the strand together with the nucleotide to which it is bound.

In the "tailing" method, at least one deoxyribonucleoside triphosphate, dideoxyribonucleoside triphosphate or ribonucleoside triphosphate is incorporated onto the 3'-OH end of either a double or single strand deoxyribo- or ribonucleic acid probe. The triphosphate used is again partly or wholly derivatized by coupling of a steroid via a bridge so that the steroid is incorporated into the strand together with the nucleotide substrate.

In the case of the phage-RNA polymerase-catalysed "transcription" method (J. Mol. Biol. 166 (1983) 477), during the deoxyribonucleic acid-dependent ribonucleic acid synthesis, the ribonucleic acid formed is derivatised. Phage-coded RNA polymerases such as phage SP6-, T7- or T3-coded enzymes are used. For this method double-stranded deoxyribonucleic acids are used which contain e.g. SP6-, T7- or T3-promotors. By addition of e.g. SP6-, T7- or T3-RNA polymerase and all four types of ribonucleoside triphosphates, starting from the homologous promotor, there is formed the ribonucleic acid strand complementary to the codogenic deoxyribonucleic acid, said ribonucleic acid strand is named the transcript. The ribonucleoside triphosphate types used as substrate are thereby incorporated. Up to four of these triphosphate types are partly or wholly derivatized by coupling of a steroid via a bridge so that the steroid bound thereto is also incorporated into the strand.

In the "photochemical" method (Nucl. Acids Res. 13 (1985) 745–761), the nucleic acid probe is irradiated in the presence of photo-digoxigenin (FIG. 2) using visible light having an ultraviolet wavelength. Splitting off of nitrogen ($N_2$) takes place, a nitrene radical resulting in which binds covalently to the nucleic acid.

For the "chemical" method, i.e. the oligodeoxyribinucleotide synthesis according to the phosphite triester method, both protected nucleoside phosphoramidites (dA/dG/dC/dT), and protected nucleoside phosphoramidites modified with substitutable amino functions (dA/dG/dC/dU) are used for precise incorporation into the oligodeoxyribonucleotide single strand. The modification of dC/dU preferably takes place in position 5 of the pyrimidine ring, that of dA/dG preferably at position 8 of the purine molecule.

After conclusion of the synthesis cycles and removal of the protective groups single-stranded oligodeoxyribonucleotides modified on the nucleobases with substitutable amino functions result which can be labelled with suitable haptens. Such haptens are steroids, preferably digoxigenin, or digoxin. Expressed another way, labelling takes place by reaction of the oligodeoxyribonucleotide with the corresponding activated esters, amides or ethers of the haptens, preferably their N-hydroxysuccinimide esters.

In a preferred embodiment of the invention, a nucleic acid probe is used, the hapten of which has been incorporated into the nucleic acid probe enzymatically with the help of DNA polymerases, RNA polymerases, reverse transcriptases or terminal transferases and corresponding hapten-modified desoxy- or ribonucleoside triphosphate substrates.

In a further preferred embodiment of the invention, a nucleic acid probe is used, the hapten of which has been incorporated photochemically with the help of photohapten and, in a third preferred embodimental form, a nucleic acid probe is used, the hapten of which has been incorporated chemically into the nucleic acid probe using oligodeoxyribonucleotide synthesis by incorporation of protected nucleoside phosphoamidites modified with substitutable amino functions and—after removal of the protective groups—by reaction of the modified oligodeoxyribonucleotide with activated esters of the heptens.

The nucleic acid probe derivatized with a steroid, prepared according to one of the described methods, is brought into contact with a denatured DNA or RNA bound to a carrier with the temperature, ionic strength, pH value and other buffer conditions—chosen based upon the length of the nucleic acid probe and the melting temperature of the hybrid to be expected resulting therefrom—so that the labelled DNA or RNA can bind to homologous DNA or RNA (hybridisation) (J. Mol. Biol. 98 (1975) 503; Proc. Natl. Acad. Sci. USA 76 (1979) 3683). Suitable as carriers are membranes or carrier materials based on nitrocellulose (e.g. Schleicher and Schüll BA85; Amersham Hybond C), reinforced or bound powdery nitrocellulose or nylon membranes derivatized with various functional groups (e.g. nitro) (e.g. Schleicher and Schüll Nytran, NEN Gene Screen, Amersham Hybond N, Pall Biodyne).

The detection of hybridized DNA or RNA then takes place in that the carrier, after thorough washing and saturation for the prevention of non-specific bindings, is incubated with an antibody or antibody fragment. The antibody or antibody fragment is directed against the steroid hapten incorporated into the nucleic acid probe. It carries a conjugated label. After the antibody incubation, it is again washed in order to detect specifically bound antibody conjugates. The determination then takes place by detecting the label of the antibody or antibody fragment according to per se known methods.

The bridge via which the hapten is bound to the nucleic acid probe can be between 4 and 32 atoms long. The bridge is built up of molecules which contain the atoms C, O, S and/or N. A greater chain length is admittedly possible but no longer very suitable since a loss of sensitivity is to be reckoned with.

In a preferred embodiment of the invention, the hapten is bound to the probe via a bridge of 11 to 16 atoms.

The bridge preferably contains both hydrophobic and hydrophilic groups.

In a preferred embodiment, the bridge is linear. In a further embodiment, the bridge consists of a branched chain and carries a hapten molecule on at least one of the chain ends. By means of the presence of several hapten molecules on the chain ends of a branched chain bridge, the detection sensitivity can be increased.

The steroid hapten is preferably bound with the bridge via an ester, amide or ether linkage.

The binding of the steroid hapten via the bridge to the nucleic acid probe is possible not only via a terminal or non-terminal phosphate group but also via a sugar residue or a base of the nucleic acid probe. However, the binding of the hapten via the bridge must take place so that hydrogen bond formation between the two complementary nucleic acid strands is not impaired.

The hapten is preferably bound via the bridge to a base or the ribose part of the nucleic acid probe. Especially preferred are cases where the hapten is bound via the bridge to the $C_5$-position of uracil or cytosine, the $C_8$-position of adenine or guanine or to the 2′-position of ribose.

The labelling of the anti-hapten antibody or of the antibody fragment takes place in per se known manner. Suitable are e.g. enzyme labels, radioactive labels, (bio)-luminescent labels or fluorescence labels. Preferred, however, is an enzyme label with enzymes such as alkaline phosphatase, peroxidase or $\beta$-galactosidase. Alkaline phosphatase is especially preferred as labelling enzyme. The determination of the alkaline phosphatase takes place via leuko systems, especially via indigoid systems, as oxidisable compounds (see EP 228 663). Tetrazolium selts serve as oxidation agents. In the case of the labelling enzyme alkaline phosphatase, a preferred redox system is X-phosphate/nitroblue tetrazolium (F. P. Altmann, Tetrazolium Salts and Formazans, Progr. Histochem. Cytochem. Vol 913 (1976), Gustav Fischer Verleg, Stuttgart, p. 1). X-phosphate is a trivial name for 5-bromo-4-chloro-3-indolyl phosphate and nitroblue tetrazolium stands for the compound 3,3′-(3,3′-dimethoxy-4,4′-biphenylene)-bis-5-phenyl-2-(4-nitrophenyl)-tetrazolium chloride (F. P. Altmann, Tetrazolium Salts and Formazans, Progr. Histochem. Cytochem. Vol. 913 (1976), Gustav Fischer Verlag, Stuttgart, pp. 1). Alkaline phosphatase splits the chromogenic substrate, in this case X-phosphate, which, due to the cleavage of the phosphate and oxidation, forms a blue, sparingly soluble dimer. Simultaneously the tetrazolium compound is also reduced to an blue, sparingly soluble formazan. This redox reaction is illustrated in FIGS. 3A and 3B.

The detection of the other suitable label systems i.e. ((bio)luminescent labelling, fluorescence labelling, radio-active labelling) is carried out according to known methods.

For the further illustration, the process according to the invention is shown in FIG. 4 schematically with the use of digoxigenin as heptan bound to dutp via a bridge of 11 atoms.

The porcess according to the invention can be used especially advantageously for:

in situ hybridization with fixed whole cells, with fixed tissue smears and isolated chromosomes (metaphase chromosomes);

colony hybridization (cells) and plaque hybridisation (phages and viruses);

Northern hydridization (RNA detection) and serum analysis (detection of viral and bacterial infections in serum, cell type analysis of cells in serum; e.g. by slot-blot analysis).

In a further preferred embodiment, before the carrying out of the determination process according to the invention, amplification is carried out of the sample, such as is described in EP-A 0200362.

A further subject of the invention is a process for the detection of nucleic acids of definite sequence (sample) which is characterized in that one treats the sample, after denaturing, with at least two oligonucleotides (primers), of which a first is, in its sequence, complementary to a partial sequence of a strand of the nucleic acid to be detected and a further one is identical to another partial sequence of the same strand of the nucleic acid to be detected (hybridisation), treats with polymerase, preferably taq-DNA polymerase, with deoxyribonucleotide and with at least one deoxyribonucleotide which contains a chemically bound steroid bound via a bridge to a position of the deoxyribonucleotide which does not participate in hydrogen bond formation, wherein said bridge is at least 4 atoms length (polymerisation) and subsequently repeats at least once the cycle consisting of denaturing, hybridization and polymerization, whereby a nucleic acid complementary to the sample results which is labelled and the so resulting labelled nucleic acid is detected via a labelled anti-hapten-antibody. In a preferred embodiment, the desoxyribonucleotide, the labelled deoxyribonucleotide and the primer are added before the denaturing reaction.

In a further preferred embodiment, after ending of the cycles, a nucleic acid, complementary to the sample and, immobilized on a solid phase is added thereto, a hybridization reaction is carried out and, after separation of solid and liquid phase, the label is determined in the solid phase.

A further object of the invention is a process for the detection of nucleic acids of definite sequence (sample) which is characterized in that one treats the sample, after denaturing, with at least two oligonucleotides (primers), of which a first one has a sequence, complementary to a first partial sequence of a strand of the sample and a further one is identical to second partial sequence of the same strand of the nucleic acid to be detected (hybridization), treats with deoxyribonucleotides, with polymerase, preferably taq-DNA polymerase (polymerization), subsequently repeats at least once the cycle consisting of denaturing, hybridization and polymerization and finally a cycle in the presence of at least one deoxyribonucleotide which contains a steroid chemically bound, at a position of the deoxyribonucleotide which does not participate in hydrogen bond formation, is bound via a bridge of at least 4 atoms length, whereby a nucleic acid complementary to the sample results which is labelled and detects the so resulting labelled nucleic acid via an in turn labelled anti-hapten antibody.

In a further preferred embodiment, after ending of the cycles, a nucleic acid, complementary to the sample and immobilized on a solid phase is added thereto, a hybridization is carried out and, after separation of solid and liquid phase, the label is determined in the solid phase.

The further conditions for this process are described, for example, in EP-A 0200362 and known under the name polymerase chain reaction (PCR).

The following Examples explain the invention in more detail in conjunction with the Figures.

Brief Description of the Drawings

FIG. 4 shows schematically a preferred embodiment of a DNA detection assay according to the invention;

FIGS. 9A and 9B show a comparison of the sensitivities of enzymatic labelling (A) according to the invention with a known chemical label (B) in the DNA detection; and FIGS. 10A–10C show the DNA sequence (SEQ ID NO: 1) of pSPT18.

FIG. 11 shows the restriction map of pSPT18.

EXAMPLE 1

Figure 1:
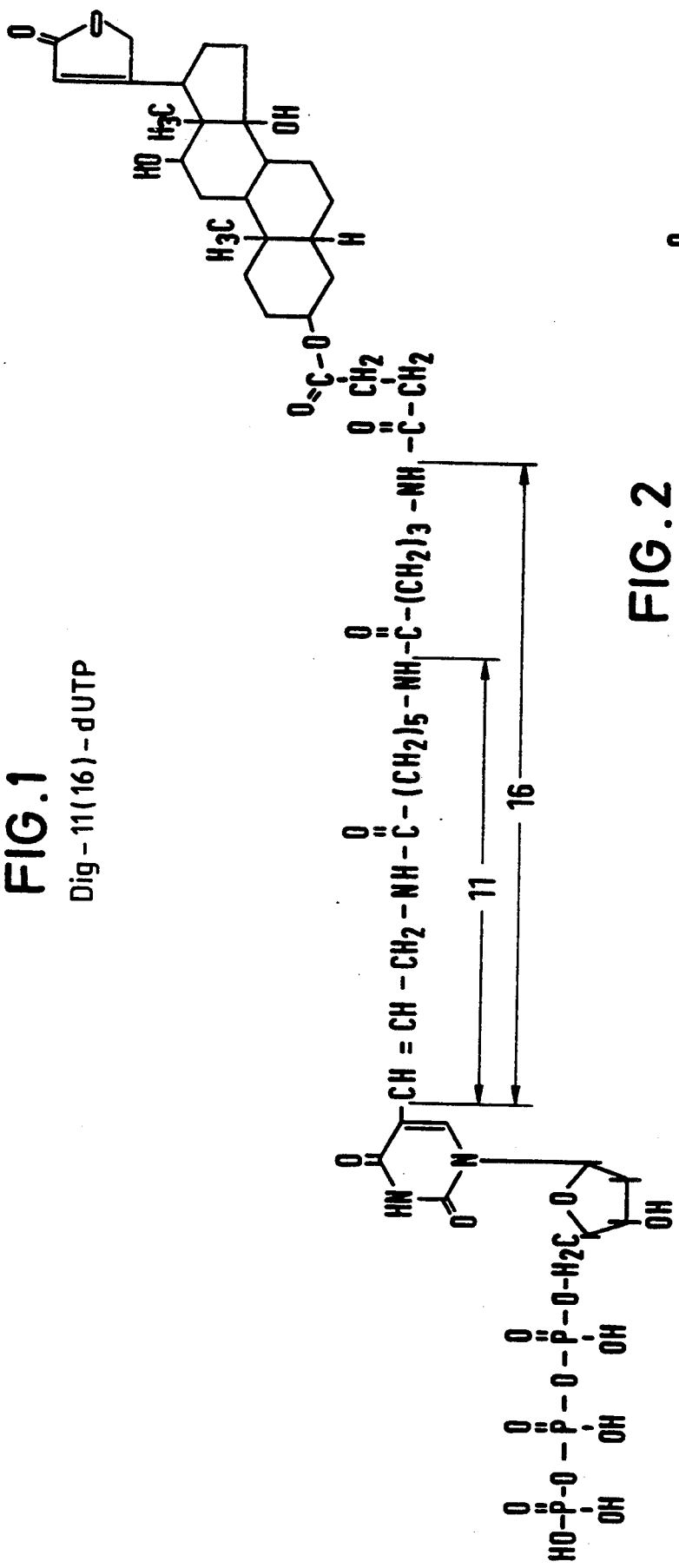
FIG. 1 shows a deoxyuridine triphosphate labelled via a bridge of 11 atoms with a digoxigenin molecule.
Figure 2:
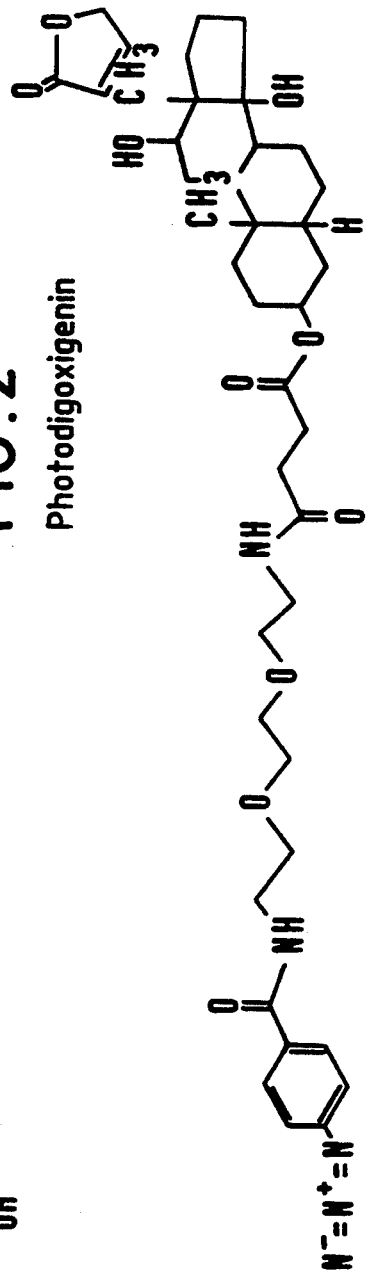
FIG. 2 shows photo-digoxigenin.
Figure 3A:
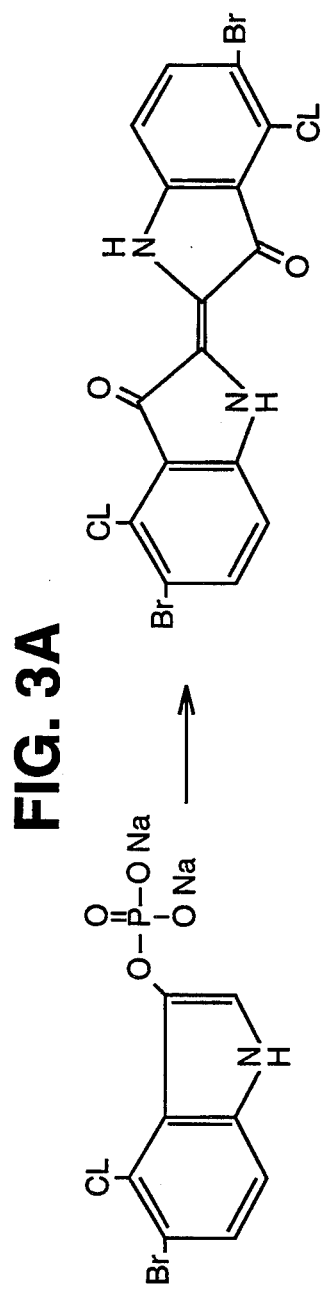
FIGS. 3A and 3B show the color reactions involved in the detection of the enzyme alkaline phosphatase via the redox system X-phosphate/nitroblue tetrazolium.
Figure 3B:
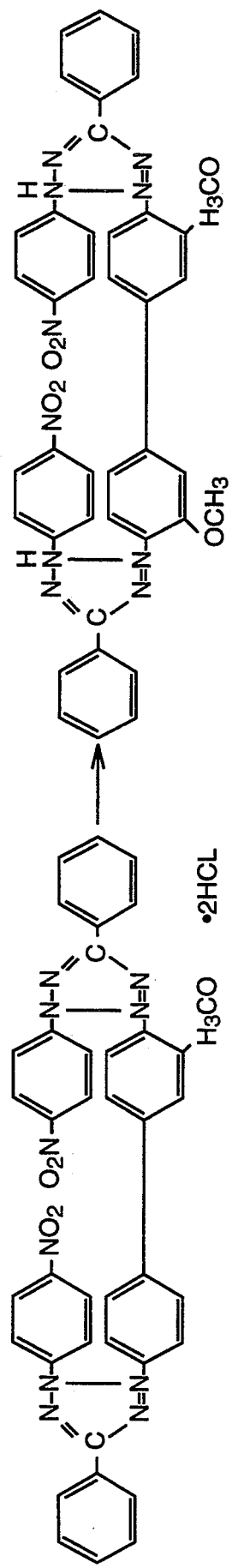

Digoxigenin-O-succinyl-[5-(amidoallyl)-2′-desoxyuridine-5′-triphosphate] tetralithium salt (Dig-4-dUTP)

$C_{39}H_{52}O_{21}N_3P_3Li_4$    M.W. 1019.5

200 mg. Digoxigenin-O-succinyl-N-hydroxysuccinimide ester (0.34 mMol) are dissolved in 7 ml. dimethylformamide and added to a solution of 186 mg. 5-allylamino-2′-deoxyuridine 5′-triphosphate tetralithium salt (0.34 mMol) in 6 ml. $H_2O$. To the reaction mixture, one adds 62 ml. 0.1M Na borate buffer, pH 8.5, and stirs for about 15 hours at room temperature.

After this time, one observes paper electrophoretically (0.05M citrate buffer, pH 5.0) under UV light, besides unreacted 5-allylamino-dUTP, a somewhat deeper running spot of the desired product.

The purification takes place as described in Example 9.

Yield: 130 mg.=37% of theory

UV spectrum (phosphate buffer pH 7.0): maxima: 220 nm., 290 nm.

EXAMPLE 2

Digoxigenin-O-succinyl-ϵ-amidocapronic acid
$C_{33}H_{49}O_9N$    M.W.: 603.8

In a 250 ml. round-bottomed flask, 5 g. digoxigenin-O-succinyl-N-hydroxysuccinimide ester (8.5 mMol) are dissolved in 150 ml. dimethylformamide (DMF) and a suspension of 1.12 g. 6-aminocapronic acid (8.5 mMol) and 1.2 ml. triethylamine in 20 ml. DMF added thereto. One stirs magnetically overnight, whereby a homogeneous solution gradually results. After this time, according to thin layer chromatography (silica gel; acetic acid ethyl ester/petroleum ether/ethanol 1:1:1, detection: spraying with a mixture of 10 ml. glacial acetic acid+0.2 ml. cond.$H_2SO_4$+0.1 ml. anisaldehyde and heating to 120° C. up to the appearance of blue-black spots; $R_f$ about 0.7; $R_f$ digoxigenin-OSu ester about 0.85), the reaction is practically complete.

One completely distils off DMF in high vacuum and dissolves the remaining oil in 50 ml. $H_2O$ with the addition of concentrated ammonia solution. Then, by addition of 225 ml. aqueous citric acid solution (100 g. citric acid/1.), the "free" digoxigeninamidocapronic acid is separated out. The resinous-viscous mass becomes solid by trituration with water; one filters off with suction, rinses several times with $H_2O$ and finally dries over $P_2O_5$ in oil pump vacuum.

Yield: 3.45 g.=68% of theory

EXAMPLE 3

Digoxigenin-O-succinyl-ε-amidocapronic acid-N-hydroxysuccinimide ester $C_{37}H_{52}O_{11}N_2$  M.W.: 700.8

In a 100 ml. round-bottomed flask, 3.45 g. digoxigenin-O-succinyl-ε-amidocapronic acid (5.7 mMol) are dissolved in 20 ml. anhydrous dimethylformamide (DMF) and successively mixed with 0.7 g. N-hydroxysuccinimide (6 mMol), as well as 1.3 g. dicyclohexylcarbodiimide (6.3 mMol). One stirs overnight at room temperature, filters off with suction the next day from separated dicyclohexylurea and strips off the DMF in oil pump vacuum. The oil remaining behind is taken up in 20 ml. acetic acid ethyl ester and stirred into about 150 ml. ice-cold (−20° C.) petroleum ether. The precipitated initially still resinous-viscous product is triturated several times with ice-cold dry petroleum ether until solidification. After drying over $P_2O_5$ in a vacuum, one obtains 3.35 g.=84% of theory Elementary analysis: C calc.: 63.4%; H calc.: 7.5%; N calc.: 4.0% . C found: 63.1%; H found: 7.7%; N found: 4.07%.

EXAMPLE 4

Digoxigenin-O-succinyl-ε-amidocaproyl-[5-(amidoallyl)-2'-desoxyuridine-5'-triphosphate] tetrasodium salt (Dig-11-dUTP)

$C_{45}H_{63}O_{22}N_4P_3Na_4$   M.W.: 1196.7

260 mg. digoxigenin-O-succinyl-ε-amidocapronic acid N-hydroxysuccinimide ester (0.37 mMol) are dissolved in in 7 ml. DMF and added to a solution of 200 mg. 5-allyl-amino-2'-deoxyuridine-5'-triphosphate tetralithium salt (0.37 mMol) in 6 ml. $H_2O$. To the mixture, one adds 62 ml. 0.1M sodium borate buffer, pH 8.5, and stirs at room temperature (about 15 hours).

After this time, using the paper electrophoresis (0.05M citrate buffer, pH 5.0), one observes in UV light, besides some unreacted allylamino-dUTP, a somewhat deeper running spot of the desired compound (alternative: thin layer chromatography (TLC) on silica gel, elution agent isobutyric acid/conc. ammonia solution/-$H_2O$=66:1:33, detection in UV or spraying with anisaldehyde reagent—see Example 2—; $R_f$ values: 5-allylamino-dUTP 0.2; Digamidocapronic acid OSu ester 0.7; Dig-11-dUTP 0.45).

For the purification, the reaction mixture is evaporated to the solid residue in oil pump vacuum, taken up in 200 ml. $H_2O$ and applied to an ion exchanger column (DEAE-Sephadex A25, $HCO_3^-$-form, column dimensions 1.5×30 cm.). After application, it is briefly washed with water, then eluted with a gradient of, in each case, 1 l. $H_2O$ to 0.4M TEAB (triethylammonium bicarbonate), pH 8. The fractions containing the pure product are combined, concentrated in a vacuum and freed from excess TEAB by repeated evaporation with methanol. One takes up the flask content in a few ml. water, passes the solution over a short cationic exchanger column DOWEX 50 WS8 (1–10 cm.) in the $Na^+$ form, washes the column until wash water (effluent) used to wash to column is nearly free of UV absorbing materials (measurement in UV at 240 nm) and evaporates in a vacuum to about 20 ml. After lyophilization, there are obtained 200 mg. (45% of theory) Dig-11-dUTP-$Na_4$ as white powder.

Analysis: $H_2O$ determination: 7.9%

Elementary analysis: (considering $H_2O$ content): C calc.: 41.8% H calc.: 5.3% N calc. 4.3% P calc.: 7.2%. C found: 41.08% H found: 5.35% N found: 4.7% P found: 7.1%.

UV spectrum (phosphate buffer pH 7.0): maxima 220 nm., 290 nm.

EXAMPLE 5

Digoxigenin-O-succinyl-γ-amidobutyric acid $C_{31}H_{45}O_9N$   M.W.: 575.8

The compound is prepared by reaction of 3 g. digoxigenin-O-succinyl-N-hydroxysuccinimide ester (5.1 mMol) with 0.63 g. 4-aminobutyric acid (6.1 mMol) as described in Example 1 for the capronic acid derivative. After reaction has taken place, the reaction mixture is evaporated in a vacuum, the residue dissolved in $H_2O$-methanol (20%) and passed over a cation exchanger column (DOWEX 50 WX8) in the $H^+$ form. Eluate and wash water (pH about 4) are evaporated, the remaining greasy-viscous residue dissolved in n-butanol and shaken out three times with water. The butanol phase contains the desired product and, after stripping off of the butanol and co-distillation three times with anhydrous DMF (removal of remaining water), used directly for the further working up to the corresponding N-hydroxysuccinimide ester (Example 6).

Yield: 2.94 g. (oil)

EXAMPLE 6

Digoxigenin-O-succinyl-γ-amidobutyric acid N-hydroxysuccinimide ester $C_{35}H_{48}O_{11}N_2$   M.W.: 672.8

2.95 g. Digoxigenin-O-succinyl-γ-amidobutyric acid (about 5.1 mMol) are, as oil from Example 5, reacted with 0.62 g. N-hydroxysuccinimide (5.4 mMol) and 1.16 g. dicyclohexylcarbodiimide (5.6 mMol) in 20 ml. anhydrous DMF as described in Example 3, and worked up. The resulting hydroxysuccinimide ester is as oil—as described in Example 7—reacted with ε-aminocapronic acid.

Yield: 3.46 g. (oil)

EXAMPLE 7

Digoxigenin-O-succinyl-γ-amidobutyryl-ε-amidocapronic acid $C_{37}H_{56}O_{10}N_2$   M.W.: 689.0

In a 250 ml. round-bottomed flask, 0.8 g. ε-amidocapronic acid (6.2 mMol) and 0.75 m. triethylamine are suspended in 12 ml. DMF and a solution of 3.46 g.

digoxigenin-O-succinyl-γ-amidobutyric acid-N-hydroxysuccinimide ester (5.1 mMol, oil from Example 6) in 90 ml. DMF added thereto. One stirs this for about 15 hours at room temperature, whereafter an almost homogeneous solution results. According to TLC (conditions described in Example 2), the reaction is almost quantitative.

The working up takes place as described under Example 5 (conversion into the "free" carboxylic acid by DOWEX 50 chromatography, extraction with n-butanol). The butanol phase contains, besides the desired product, some additional polar and non-polar material and is, therefore, purified by chromatography on silica gel 60 (column 40×3 cm., elution agent acetic acid ethyl ester/petroleum ether 50/75/ethanol 1:1:1). After combining of the acidic fractions and evaporation, one obtains, as oil 1.48 g. = 42% of theory

EXAMPLE 8

Digoxigenin-O-succinyl-γ-amidobutyryl-ε-amidocapronic acid N-hydroxysuccinimide ester $C_{41}H_{59}O_{12}N_3$   M.W.: 785.8

0.2 g. Digoxigenin-O-succinyl-γ-amidobutyryl-ε-amidocapronic acid (oil from Example 7, about 0.29 mMol) are reacted with 0.034 g. N-hydroxysuccinimide (0.3 mMol) and 66 mg. dicyclohexylcarbodiimide (0.32 mMol) in 8 ml. anhydrous DMF as described in Example 3 and worked up. The oily residue obtained was not obtained in solid form by repeated trituration with cold petroleum ether and was, therefore, after stripping off of the solvent, brought directly to reaction—as described in Example 9—with 5-aminoallyl-dUTP.

Yield: 0.25 g. (oil)

EXAMPLE 9

Digoxigenin-O-succinyl-γ-amidobutyryl-ε-amidocaproyl[5-amidoallyl)-2'-desoxyuridine-5'-triphosphate]-tetralithium salt (Dig-16-dUTP)

$C_{49}H_{70}O_{23}N_5P_3Li_4$   M.W. 1217.7

250 mg. Digoxigenin-O-succinyl-γ-amidobutyryl-ε-amidocapronic acid N-hydroxysuccinimide ester (oil from Example 8, 0.3 mMol) are dissolved in 7 ml. DMF and added to a solution of 210 mg. 5-allylamino-2'-desoxyuridine-5'-triphosphate tetralithium salt (0.38 mMol) in 6 ml. $H_2O$. To the reaction mixture one adds 62 ml. 0.2M sodium borate buffer, pH 8.5, and stirs for about 15 hours at room temperature. The course of the reaction is monitored as described under Example 4.

For the purification, the batch is evaporated to a solid residue in oil pump vaccum, dissolved in about 200 ml. $H_2O$ and applied to an ion exchanger column (DEAE-Sephadex A-25, Cl$^-$ form, column dimensions 1.5×30 cm.). After washing with $H_2O$, it is eluted with a linear gradient of 2 l. $H_2O$ to 2 l. 0.3M LiCl. The fractions containing the pure product are combined, concentrated in a vacuum to such an extent that no more $H_2O$ passes over and the concentrate precipitated subsequently in an acetone-ethanol mixture (3:1) by stirring. One centrifuges off from supernatant, washes with ethanol until Cl$^-$ free and dries in a vacuum over $P_2O_5$/KOH.

Yield: 250 mg. = 68% of theory

Analysis: $H_2O$ determination: 6.3%

Elementary analysis (considering $H_2O$ content): C calc.: 45.5% H calc.: 5.7% N calc.: 5.4% P calc.: 7.2%. C found: 45.1% H found: 5.6% N found: 5.6% P found: 7.0%.

UV spectrum (phosphate buffer pH 7.0); maxima: 220 nm (shoulder), 289 nm

EXAMPLE 10

Digoxigenin-O-succinyl-ε-amidocaproyl-[5-(amidoalllyl)uridine-5'-triphosphate] tetralithium salt $C_{45}H_{63}O_{23}N_4P_3Li_4$   M.W.: 1148.5

The compound is prepared analogously to Example 4 by reaction of 520 mg. digoxigenin-O-succinyl-ε-amidocapronic acid-N-hydroxysuccinimide ester (0.74 mMol) with 416.5 mg. 5-allylamino-UTP tetralithium salt (0.74 mMol). As a variation, the ion exchange chromatography takes place according to Example 9 on DEAE-Sephadex A-25 in the Cl$^-$ form.

Yield: 560 mg. = 66% of theory

Analysis: $H_2O$ determination: 8.1%

Elementary analysis (having regard to the $H_2O$ content): C calc.: 43.5% H calc.: 5.47% N calc.: 4.5% P calc.: 7.47%. C found: 43.1% H found: 5.3% N found: 4.5% P found: 7.35%.

UV spectrum (phosphate buffer pH 7.0): corresponds to Dig-11-dUTP.

EXAMPLE 11

Digoxigenin-O-succinyl-γ-amidobutyryl-ε-amidocaproyl-[5-(amidoallyl)-uridine-5'-triphosphate]-tetralithium salt (Dig-16-dUTP)

$C_{49}H_{70}O_{24}N_5P_3Li_4$   M.W.; 1233.7

The compound is prepared by reaction of 250 mg. digoxigenin-O-succinyl-γ-amidobutyryl-ε-amidocapronic acid N-hydroxysuccinimide ester (0.3 mMol, obtained according to Example 8) with 214 mg. 5-allylamino-UTP-Li$_4$ (0.38 mMol) analogously to Example 9.

Yield: 218 mg. = 59% of theory

Analysis: $H_2O$ determination = 7.2%

Elementary analysis (considering the $H_2O$ value): C calc.: 44.45% H calc.: 5.67% N calc.: 5.3% P calc.: 7.1%. C found: 44.3% H found: 5.5% N found: 5.3% P found: 7.1%.

UV spectrum (phosphate buffer pH 7.0): corresponds to Dig-16-dUTP

EXAMPLE 12

Preparation of N-azidobenzoyl-1,8-diamino-3,6-dioxaoctane 5.20 g. (20 mmol) Azidobenzoic acid N-hydroxysuccinimide ester (firm Pierce, D-6054 Rodgau 1) are dissolved in anhydrous ethyl acetate and mixed with 29.3 ml. (200 mmol) 1,8-diamino-3,6-dioxaoctane. One allows the reaction mixture to stir in the dark for 20 hours at 20° C. The solvent is removed in a vacuum and the oily residue dissolved in 300 ml. water. The product is extracted from the aqueous phase with 2 l. of toluene in a perforator, whereby one envelops the apparatus with aluminium foil. The extraction is ended after about 16 hours. The organic phase is freed from solvent in a vacuum and the product purified by preparative column chromatography on silica gel (column 80×10 cm., eluant: chloroform/methanol/conc. ammonia solution 65:30:5) and, after evaporation of the solvent, dried in a high vacuum. Yield: 3.2 g. (55%); colourless, viscous oil.

EXAMPLE 13

Preparation of digoxigenin-3-hemisuccinate [N'-(4-azidobenzoyl)]-8-amino-3,6-dioxaoctylamide (photodigoxigenin)

2.93 g. (10 mmol) of the product of Example 12 are dissolved in 200 ml. anhydrous dioxan and mixed with 5.87 g. (10 mmol) digoxigenin-3-hemisuccinate N-hydroxysuccinimide ester (see: G. C. Oliver, Jr., Brent, M. Parker, D. L. Brasfield and Ch. W. Parker, J. Clin. Invest. 47 (1986), 1035). One stirs this for 20 hours at room temperature, removes the solvent in a vacuum and separates off the resultant product by preparative middle pressure liquid chromatography (column volume: 1640 ml., Labochrom Reversed-Phase-Silica HD-SIL-18-30-60, eluent methanol/water 7:3+1% glacial acetic acid). After collection of the appropriate fractions, the solvent is removed in a vacuum and the oily residue dissolved in dioxan. After lyophilisation and washing with 100 ml. diisopropyl ether, the product digoxigenin-3-hemisuccinate [N'9(4-azidobenzoyl)]-8-amino-3,6-dioxaoctylamide is obtained as colourless, slightly sticky solid material which is dried in a high vacuum.

Yield: 4.9 g. (64%)

IR (acetone):=2150, 1728, 1639 cm$^{-1}$.

EXAMPLE 14

Labelling of a Nucleic Acid Probe According to the "Random Primed" method

1 μg. of the linear DNA to be labelled was denatured in one volume of 10 μl. by 5 minutes boiling and subsequent quenching on ice. Thereafter, in a reaction vessel, 1 μl. each of a 2 mmol/l. solution of deoxyadenosine triphosphate, deoxycytidine triphosphate and deoxyguanosine triphosphate and the denatured DNA were combined. To this was added 1 μl. of a solution which contained 1.4 mmol/l. desoxythymidine triphosphate and 0.6 mmol/l. digoxigenin-ll-dUTP prepared as in Example 4. Thereafter, 2 μl. of a so-called reaction mixture were added thereto. The reaction mixture contained, as the most important component, the so-called "random hexanucleotide". It is thereby a question of chemically synthesised oligonucleotides of 6 base length, whereby in the case of the synthesis, in each step all 4 nucleotides (A, C, G and T) are made available and thus a mixture of all possible oligonucleotide sequences results. The chemical composition of the reaction mixture was: Tris-HCl, 0.5 mol/l.; MgCl$_2$, 0.1 mol/l.; dithioerithritol, 1 mmol/l.; bovine serum albumin, molecular biological quality, 2 mg./ml.; random hexanucleotide, 3.125 mg./ml.; pH 7.2 (20° C.)); finally, 1 μl. Klenow polymerase, corresponding to 2 Units, was added thereto and the mixture brought with sterile water to 20 μl. end volume and incubated for 1 hour at 37° C.

Thereafter, the reaction was stopped by the addition of 2 μl. 0.2 mol/l. EDTA (ethylenedinitrilo-tetraacetic acid), pH 8.0 and non-incorporated deoxyribonucleoside triphosphates separated off by ethanol precipitation. For this purpose, to the incubation batch were added 2 μl. LiCl, 4 mol/l. and 60 μl. absolute ethanol precooled to −20° C., mixed and the precipitation batch incubated at −70° C. for 30 minutes or at −20° C.

overnight. Subsequently, it was centrifuged at 12000×g (force of gravity) for 10 minutes, the supernatant decanted off, the precipitate briefly washed with cold 70% ethanol and finally dried in a vacuum. The labelled purified DNA was finally resuspended in 50 μl. TE buffer (Tris-HCl, 10 mmol/l.; EDTA, 1 mmol/l.; pH 8.0).

EXAMPLE 15

Labelling of a Nucleic Acid Probe According to the "Nick Translation" Method

1 μg. of the DNA to be labelled was mixed with, in each case, 1 μl. of a 0.4 mmol/l. solution of deoxyadenosine triphosphate, deoxycytidine triphosphate and deoxyguanosine triphosphate.

There was then added 1 μl. of a solution which contained 0.35 mmol/l. desoxythymidine triphosphate and 0.15 mmol/l. Dig-11-dUTP prepared as in Example 4. Furthermore, 2 μl. of a 10 fold concentrated buffer solution (Tris-HCl, 0.5 mol/l.; MgC$_{12}$, 0.1 mol/l.; dithioerythritol, 1 mmol/l.; pH 7.5), as well as 2 μl. of an enzyme solution containing 2 Units of DNA polymerase I and 1.6 Units of DNAse I, were added thereto, made up with sterile double distilled water to an end volume of 20 μl. and the batch incubated for 60 minutes at 14° C.

The reaction was stopped with EDTA as in Example 13 and the labelled DNA purified and dissolved as described above.

EXAMPLE 16

Labelling of a Nucleic Acid Probe With The "Tailing" Method

In the case of the 3'-end labelling with the help of the enzyme terminal transferase, digoxigenin-11-dideoxyuridine triphosphate was used. This was synthesised as described in Example 4, with the exception that, as starting substance, 5-allylamino-2',3'-dideoxyuridine-5'-triphosphate tetralithium salt was used instead of the 2'-deoxyuridine salt. The labelling reaction was carried out as follows:

In a reaction vessel were mixed: 25 μl. labelling buffer (potassium cacodylate, 200 mmol/l.; Tris-HCl, 50 mmol/l.; bovine serum albumin, 0.4 mg./ml.; pH 7.2), 5 μl. 25 mmol/l. CoCl$_2$ solution, 1.5 μg. Hae II-cleaved pBR322 DNA and 5 μl. corresponding to 25 Units of terminal transferase. The volume was made up to 48 μl. with sterile double distilled water and finally 2 μl. of a 0.1 mmol/l. solution of digoxigenin-11 dUTP added thereto.

After mixing and centrifuging, the reaction was incubated at 37° C. for one hour.

The stopping of the reaction and the separation of non-incorporated nucleotides took place as described above in Example 14.

EXAMPLE 17

Labelling of a nucleic acid probe with the "transcription" method

Figure 5:
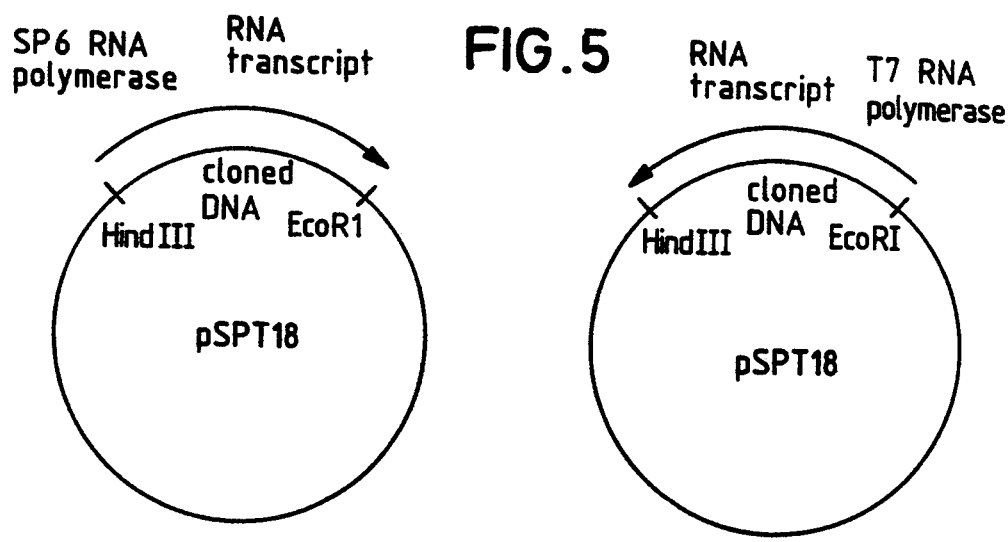
FIG. 5 indicates the preparation of an RNA transcript using SP6 or T7 RNA polymerase-catalysed transcription with plasmids pSPT18.
Figure 6:
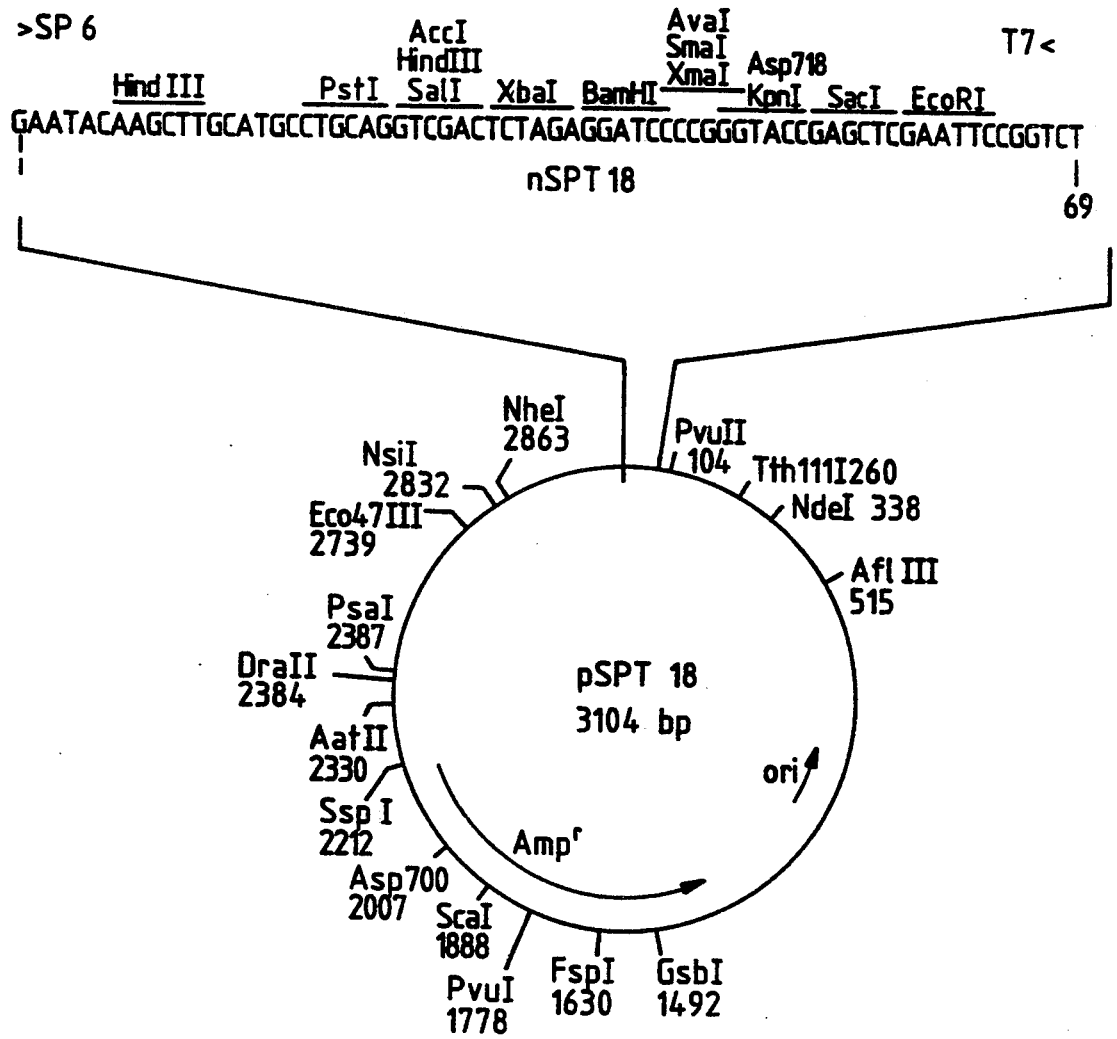
FIG. 6 shows the different DNA regions of the plasmid pSPT18.
Figure 7:
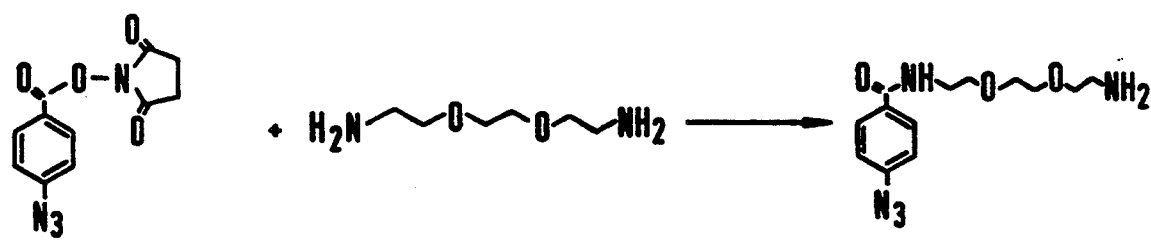
FIG. 7 shows a synthesis scheme for the preparation of photo-digoxigenin.
Figure 7:
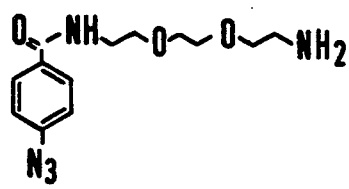
Figure 7:
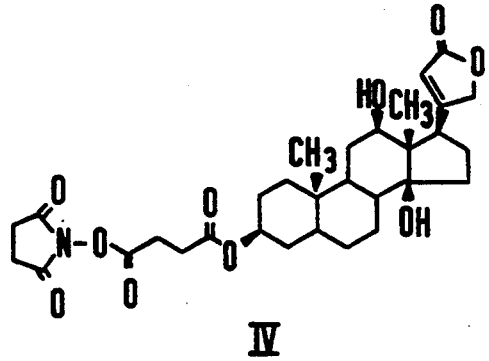
Figure 7:
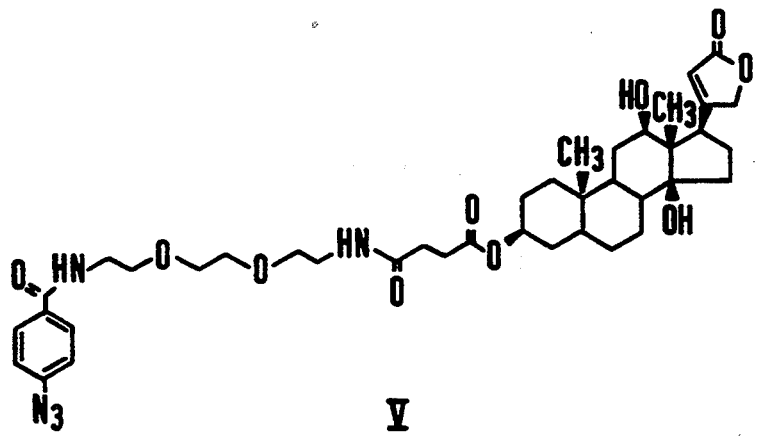

The principle of the reaction is to be seen from FIG. 5. The DNA used for the labelling was inserted into the transcription vector pSPT18 (FIGS. 6 and 10). The vector contains a promotor for the SP6 and a promotor for the T7 RNA polymerase. Before the labelling reaction, the DNA was linearized at a position outside of the inserted DNA sequence and the promotors, as well as the promotors and the DNA sequence-connecting sequences. To 1 μg. of the linearized substrate DNA was added in in 1 μl. of each of a 10 mmol/l. solution of adenosine triphosphate, cytidine triphosphate and guanosine triphosphate. To this was added 1 μl. of a solution which contains 6.5 mmol/l. uridine triphosphate and 3.5 mmol/l. digoxigenin-11-UTP. Digoxigenin-11-UTP is prepared in Example 10 similarly to digoxigenin-11-dUTP in Example 4 except that, as starting substance, instead of allylaminodesoxy uridine salt, there is used allylaminouridine salt.

Furthermore, to the batch was added 2 μl. of a 10 fold concentrated buffer (Tris-HCl, 0.4 mol/l.; MgC$_{12}$, 60 mmol/l.; dithiothreitol, 50 mmol/l.; spermidine, 40 mmol/l.; pH 7.2), the volume made up to 19 μl. with sterile twice distilled water and finally the reaction started by the addition of 1 μl., corresponding to 10 Units, of RNA polymerase (SP6 or T7).

After brief centrifugation, the batch is incubated at 37° C. for one hour.

The substrate DNA was subsequently broken down by addition of 1 μl. DNAse I, RNAse-free, corresponding to 10 Units, for 15 minutes at 37° C.

The reaction was stopped by the addition of 2 μl. 0.2 mol/l. EDTA, pH 8.0. The digoxigenin-labelled RNA probe obtained was purified by extraction with 1 volume of phenol and by subsequent ethanol precipitation from proteins and nucleotides and finally dissolved in sterile buffer (Tris-HCl, 10 mmol/l.; EDTA 1 mmol/l.; pH 8.0).

EXAMPLE 18

Labelling of a Nucleic Acid Probe with the "Photochemical" Method

The purified DNA solution (no organic buffer), preferably in a concentration of 0.5 to 1.0 μg./ μl., was mixed in an Eppendorf reaction vessel in semi-darkness with the same volume of a 1 mg./ml. photodigoxigenin solution (Example 13). The mixture was irradiated, with ice cooling, with a Philips HPLR 400 W lamp at 10 cm. distance for 10 to 30 minutes from above through the vessel opening. The reaction mixture must thereby remain cold.

After the reaction, it was made up with 0.1M Tris-HCl, pH 9.0, 1.0 mM EDTA to 100 μl.

The solution was shaken out with 100 μl. butan-2-ol, briefly centrifuged and the upper butanol phase removed.

The buten-2-ol extraction was repeated once, the aqueous phase should now be concentrated to 30 to 40 μl.

After addition of carrier DNA(only in the case of small amounts of DNA), by addition of 5 μl. 3M sodium acetate or of a corresponding salt (e.g. 4M LiCl) and 100 μl. ethanol, it was precipitated overnight at −20° C.

After centrifuging at 4° C. for 15 minutes in an Eppendorf centrifuge, the pellet was washed with cold 70% ethanol, dried and dissolved in 0.1 mM EDTA.

EXAMPLE 19

Hybridization with labelled DNA probe

For the hybridization, a nitrocellulose filter (Schleicher & Schüll, BA 85) with DNA fixed thereon was used. For the pre-hybridization, the filter was first incubated at 65° C. in a solution consisting of NaCl, 0.75 mol/l.; Na citrate, 75 mmol/l; casein, 0.5% (w/v); lauryl sarcosine, 0.1% (v/v); sodium dodecyl sulphate, 0.02% (w/v); pH 7.0 (20° C.). Subsequently, the solution was replaced by a fresh solution of the same composition, to which was additionally added 100 ng./ml. of the labelled, freshly denatured DNA prepared as in Example 14 to 16 or 18. There followed a renewed incubation at 65° C. for 14 hours. Thereafter, non-specifically bound DNA was removed by two washing steps, namely, first with a solution of NaCl, 0.3 mol/l.; Na citrate, 30 mmol/l; Na dodecyl sulphate, 0.1% (w/v); pH 7.0 for 2×5 minutes at room temperature and subsequently with a solution of NaCl, 15 mmol/l., Na citrate 1.5 mmol/l.; Na dodecyl sulphate, 0.1% (w/v); pH 7.0 for 2×15 minutes at 65° C.

EXAMPLE 20

Hybridization with a labelled RNA probe

Hybridization and subsequent washings were carried out exactly as described in Example 19 on the basis of the DNA probe. Only instead of the denatured labelled DNA probe described in the Example a freshly denatured RNA probe labelled as in the above Example 17 was used.

The concentration of the digoxigenin-labelled RNA in the hybridization solution was so chosen that, the transcripts of 100 ng. substrate DNA were used per ml of hybridization solution.

EXAMPLE 21

Detection with the help of the detection system alkaline phosphatase/X phosphate/nitroblue tetrazolium The hybridized filter from Example 19 or 20 was first washed for 1 minute in Tris-HCl, 0.1 mol/l. pH 7.5; NaCl, 0.15 mol/l. For the blocking of non-specific binding positions, the filter was subsequently incubated with 0.5% (w/v) casein in Tris-HCl 0.1 mol/l., pH 7.5; NaCl, 0.15 mol/l. for 40 minutes with gentle rotation.

Thereafter, the antibody binding reaction was carried out. For this purpose, the filter was incubated with anti-digoxigenin/alkaline phosphatase conjugate, 150 Units/ml. in Tris-HCl, 0.1 mol/l.; pH 7.5; NaCl, 0.15 mol/l. for 20 minutes. Non-specifically bound protein was then removed by 2×15 minutes washing with the same buffer. Thereafter, the filter was reequilibrated to pH 9.5 in Tris-HCl, 0.1 mol/l. pH 9.5; NaCl 0.1 mol/l.; MgCl$_2$, 50 mmol/l. for 5 minutes, the alkaline phosphatase having its activity optimum at higher pH values. The detection of bound antibody conjugate and thus of the hybridized labelled DNA took place by a colour reaction catalysed by alkaline phosphatase. For this purpose, the filter was incubated in Tris-HCl, 0.1 mol/l. pH 9.5; NaCl, 0.1 mol/l.; MgCl$_2$, 50 mmol/l., whereby, per 10 ml. of solution, 45 μl. nitroblue tetrazolium solution (75 mg./ml. in dimethylformamide, 70% v/v)) and 35 μl. of an X phosphate solution (50 mg./ml. 5-bromo-4-chloro-3-indolyl phosphate in dimethylformamide) were added thereto.

The colour reaction took place with substantial exclusion of oxygen in that one kept the membrane with this solution in a foil (normal cooking or freezing foil) welded and in the dark. The colour reaction commences very quickly but could, however, increase in intensity over several days. Documentation of the result was obtained by photography or photocopying of the moist filter. The filter was then dried and stored. The colour is maintained but fades somewhat. It can be intensified by moistening of the filter.

EXAMPLE 22

Figure 8:
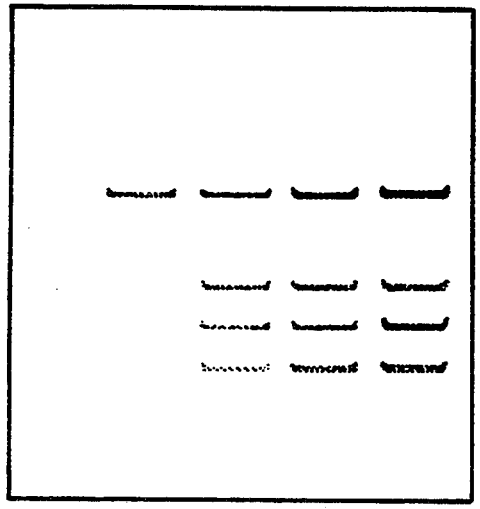
FIG. 8 shows a comparison of the sensitivities of the detection according to the invention with digoxigenin as hapten as compared to detection via biotin/streptavidin of placental DNA according to Southern blotting and hybridization.
Figure 8:
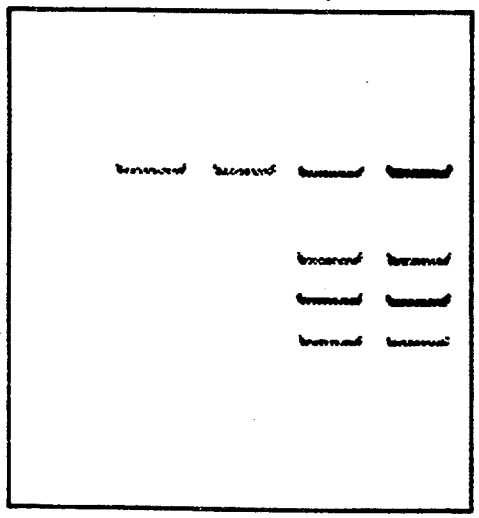

Comparison of the sensitivities and of the background in the DNA detection (Southern blot) in the case use of DNA labelled a) enzymatically with digoxigenin according to Example 14 and b) enzymatically with biotin. I. Human placental DNA was cleaved with the restriction enzyme Eco RI. Differing amounts thereof were separated electrophoretically in an agarose gel and subsequently transferred according to the method of Southern (J. Mol. Biol. 98 (1975) 503) to a nitrocellulose membrane. The DNA on the membrane was fixed by 2 hours baking at 80° C. in a vacuum cabinet. The membranes were hybridized with a labelled DNA fragment which corresponds to the cDNA of the human tissue plasminogen activator (Pennica D. et al. Nature 301 (1983) 214). The human tissue plasminogen activator gene is present once in the human genome. The cDNA of this gene hybridizes with the corresponding bands of the genome. On the one hand, the DNA fragment was labelled with digoxigenin as in Example 14, hybridized with 100 ng./ml. labelled DNA as in Example 19 and the hybrids detected as described in Example 21. On the other hand, the fragment was labelled in an analogous process with biotin. Biotin 16-dUTP (Brigati et al., Virology 126 (1983) 32–50) was used. The DNA on the membrane was hybridized with 50 $\mu$g./ml. labelled DNA. Otherwise, the procedure was according to Example 19. The detection took place as described in Example 21 with the exception that a streptavidin-alkaline phosphatase conjugate was used. In comparison with the process described in the literature for the biotin system, the here-described system of the biotin labelling ("random primer" labelling, mixing biotin 16-dUTP/dTTP, prehybridization with the solution described in Example 19, hybridization with the given concentration of DNA, blocking with the solution described in Example 21) shows smaller background and higher sensitivity. Nevertheless, in the case of the described use of digoxigenin instead of biotin in the optimised system, a distinct further reduction of the background is obtained, whereby the sensitivity is maintained (FIG. 8).

EXAMPLE 23

Comparison of sensitivities in the DNA detection (Southern blot) using DNA labelled a) enzymatically with digoxigenin according to Example 14 and b) chemically according to Example 1 and 2 of European Patent Application 0173251 with digoxigenin.

pBR328 DNA was cleaved separately with the restriction enzymes Bgl I and Hinf I. The fragments obtained were mixed in equal parts. Thereafter, the mixture contains 15 pBR328 fragments of the size: 2176, 1766, 1230, 1033, 653, 517, 453, 394, 298 (2x), 234 (2x), 220 and 154 (2x) bp.

Differing amounts of the fragments were then separated electrophoretically in an agarose gel and subsequently transferred to a nitrocellulose membrane according to the method of Southern (J. Mol. Biol. 98 (1975) 503). After fixing of the DNA fragments by heating of the membrane in a vacuum to 80° C., this was hybridized with 100 ng./ml. of DNA digoxigenin-labelled according to Example 14 as described in Example 19. The detection of the hybrids took place exactly as described in Example 21. As FIG. 9A shows in combination with Table I, the fragments can be detected down to an amount of 1 to 0.1 pg.

As comparison, pBR328 DNA was cleaved with Nci I. There result 10 fragments of the size: 810, 724, 696, 597, 522, 507, 364, 351, 244 and 92 bp. Here, too, different amounts of DNA were electrophorised and subsequently transferred according to Southern to a nitrocellulose membrane. The membrane was then hybridised as in Example 19. Here, however, 200 ng./ml. of labelled pBR322 DNA were used for the hybridization as in Example 1 and 2 of EPA 0173251. The DNA of plasmid pBR328 DNA differs from the pBR322 DNA used as probe merely by the 810 bp sized Nci I fragment which pBR328 contains but pBR322 does not. Thus, this is not detected in the hybridization. After the hybridization, the hybrids were detected precisely as described in Example 21. As FIG. 9B shows, in conjunction with Table II, according to this method, only DNA fragments can be detected to an amount of 25 to 2.5 pg. Thus, due the enzymatic labelling, in comparison with the chemical labelling, there is achieved a sensitivity of DNA detection higher by a multiple (factor 25).

TABLE I

Amount of the DNA in the individual fragments of a mixture of pBR 328 Bgl II fragments and applied amount (pg.) of DNA

| fragment size | 125 | 25 | 5 | 1 | |
|---|---|---|---|---|---|
| 2167 bp≙22.08% | 27.6+ | 5.5+ | 1.1+ | 0.22+ | amount in pg. corresponding to the individual bands |
| 1766 bp≙17.99% | 22.5+ | 4.5+ | 0.9+ | 0.18+ | |
| 1230 bp≙12.53% | 15.7+ | 3.1+ | 0.6+ | 0.12 | |
| 1033 bp≙10.53% | 13.2+ | 2.6+ | 0.5+ | 0.1 | |
| 653 bp≙6.65% | 8.3+ | 1.66+ | 0.3 | 0.07 | |
| 517 bp≙5.27% | 6.6+ | | | | |
| 453 bp≙4.62% | 5.78+ | | | | |
| 394 bp≙4.01% | 5.0 | | | | |

+Bands which on the blot in FIG. 9A are clearly coloured.

TABLE II pBR328, Nci I cleavage: Amount of the DNA in the individual fragments in dependence upon the total DNA amount per path

| fragment size (bp) | proportion, % of the total DNA | applied amount of DNA (pg.) | | | |
|---|---|---|---|---|---|
| | | 100 | 200 | 1000 | 2000 |
| 810 | 16.5 | 16.5 | 33.0 | 165.1 | 330.1 |
| 724 | 14.8+ | 14.8+ | 29.5+ | 147.5+ | 295.1+ |
| 696 | 14.2+ | 14.2+ | 28.4+ | 141.8+ | 283.7+ |
| 597 | 12.2+ | 12.2+ | 24.3+ | 121.7+ | 243.3+ |
| 522 | 10.6+ | 10.6+ | 21.3+ | 106.4+ | 212.8+ |
| 507 | 10.3+ | 10.3+ | 20.7+ | 103.3+ | 206.6+ |
| 364 | 7.4 | 7.4 | 14.8+ | 74.2+ | 148.4+ |
| 351 | 7.2 | 7.2 | 14.3+ | 71.5+ | 143.1+ |
| 244 | 5.0 | 5.0 | 9.9 | 49.7+ | 99.4+ |
| 92 | 1.9 | 1.9 | 3.7 | 18.7+ | 37.5+ |

The fragments still well visible on the moist membranes of the blot of FIG. 9B are marked with +.

EXAMPLE 24

Detection of HPV Sequences in Fixed HeLa and SiHa Cell Lines by In Situ Hybridization With the process according to the invention in situ hybridization with carrier-fixed cells and cell smears were carried out.

For the non-radioactive HPV detection, two cell lines were used:

SiHa cells (2–3 copies HPV/cell) ATCC No. HTB 35 (Biology 159 (1987) 389–398)

HeLa Cells (100–200 copies HPV/cell) ATCC No. CCL 2 (Human Genetics 77 (1987) 251–255)

DNA probe:

HPV-DNA (sequence cf. Progress med. Virol. 32 (1985) 15 et seq.)

Label:

Biotin-11-dUTP (Blugene nonradioactive DNA detection kit, order No. 8279SA of the firm Gibco/FRG)

Digoxigenin-dUTP (prepared and labelled according to Example 4 and 14).

$^{35}$S-dATP (Amersham-Buchler, order No. SJ1304), specific activity 1200 Curie/mmol).

Hybridization and washing conditions according to J. mol. Biol. 3 (1961) 585 et seq.

Cells of the said cell lines are seeded out on HCl-cleaned (0.1N HCl, 10 min. at 100° C. in phosphate buffered saline (PBS)), washed and subsequently UV-irradiated microscope slides in plastic culture dishes. As culture medium minimal essential medium (MEM) was used with 5% fetal calf serum (MEM, PBS, SSC cf. Science 130 (1950) 432 et seq.).

After formation of a semi-confluent cell covering, the microscope slides were taken from the plastic dishes and washed several times with PBS.

Fixing of the cells on the glass surface followed. For this purpose, 4% paraformaldehyde was used (5 min. at room temperature, then washing in 2×SSC).

Hybridization took place under siliconized cover glasses. For this purpose, the DNA of the HPV probe in hybridization solution (non-radioactive probe: 20 ng./hybridization region, isotope-labelled probe: 3 ng. with five times $10^5$ cpM/hybridization region) was applied to the cell covering. (The prehybridization took place as described in Example 19). After laying on of the cover slip, this was sealed (e.g. with Fixogum ® of Marabu). The denaturing of the DNA in the cells and the DNA probe then took place by laying the microscope slide on a hot oven for 3 to 5 minutes. A temperature of 90°–92° C. was hereby measured on the microscope slide by means of a temperature sensor. The microscope slides are then briefly laid on ice and subsequently incubated overnight in a humid chamber (2×SSC).

After removal of the cover slips, it was washed with 2×SSC, 0.1% SDS, 2×15 min. at room temperature and 0.2×SSC, 0.1% SDS, 2×15 min. at 52° C.

In the case of the non-radioactive system, one then worked according to Example 21 or in the biotin system (cf. working instructions of the BRL kit: blocking with 3% bovine serum albumin, addition of a conjugate of streptavidin and alkaline phosphatase, as well as substrate mixture). In the dioxigenin system, the procedure was according to Example 21. The enzyme reaction was observed for up to 48 hours.

As probe a digoxigenin-labelled subfragment of the genome of HPV Type 18 (PNAS 80 (1983) 3812–3815, New Engl. J. Med. 310 (1984) 880–883) was used. It is shown that with the digoxigenin system in the HeLa cells, the coloration of the nuclear region is clearly recognized. After DNase digestion before hybridization, only a small non-specific background remained. The omission of the labelled probe leads to no coloration. Also in the case of SiHa cells which only have integrated two to three copies of HPV per cell in the genome, the HPV detection takes place overnight. In the case of these cells, too, the nuclear region is preponderantly coloured. DNase digestion leads to small background. The omission of the labelled sample leads to non-coloured cells.

The situation is otherwise in the case of the use of biotin-labelled probes. The biotin system admittedly leads to a weak coloration of HeLa Cells, with SiHa cells however the cytosol is preponderantly non-specifically coloured. The nuclear region is only slightly coloured. The non-specificity of the biotin detection system is also shown by the fact that the same coloration of the cytosol also takes place without biotin-labelled probe but after addition solely of a streptavidin-alkaline phosphatase conjugate and of the corresponding colour material system.

With radioactively-labelled $^{35}$S probes, the HPV detection in HeLa and SiHa cells is admittedly possible but an autoradiography of 2–3 weeks is necessary therefor.

In the case of in situ hybridization on fixed cells, the process according to the invention has, in comparison with the process with the use of radiactively-labelled probes, the advantage of time saving, in comparison with the process with the use of biotin-labelled probes the advantage of higher sensitivity and clearly higher specificity.

Besides in situ hybridization in fixed cells, with the system according to the invention an HPV detection in tissue smears, e.g. in HPV-infected tissue from the vaginal region is also possible.

EXAMPLE 25

Detection of SUP 6 tRNA by Colony Hybridization

A 750 bp Bam HI fragment of SUP 6 tRN (Science 209 (1978), 1396–1460) from Saccharomyces cervisiae was cloned into pUC19 (Gene 133 (1985), 103–119) and transformed in E. coli HB 101 (DSM 1607). As control, the pUC-19 vector alone was transformed in E. coli HB 101. Thereafter, alternatingly, insert-containing bacteria were smeared on to nitrocellulose beside control transformants. After incubation for 5 hours at 37° C. on agar plates with nutrient medium, the E. coli cells were treated with alkali, washed and the liberated DNA fixed by the membrane by cross-linking at 354 nm. Subsequently, washing again followed for 3 hours at 50° C., prehybridization and hybridization analogous to Example 19 with digoxigenin-labelled SUP tRNA Bam HI fragments (preparation analogous to Example 14). One hour is sufficient for the subsequent detection.

The insert-containing bacteria each give clear signals, the control transformants are not detected. Longer detection times strengthen the positive signals but the control transformants remain background-free even in the case of comparatively long detection.

EXAMPLE 26

In Situ Hybridization of Lambda Plaques

Lambda gt10 phases (Mol. Gen. Genet. 150 (1977), 53) with a complete cDNA of human urokinase as insert were incubated on indicator plates so that about 500 single plaques were visible on a plate. On a further plate was plated out a mixture of urokinase recombinants and an equal phage amount consisting of a heterogenous population of a gene bank. This plate served as control since only the urokinase recombinants should give a positive signal with a urokinase cDNA as hybridization probe. From all plates two nitrocellulose impressions as described in Science 196 (1977), 180 were produced and hybridized.

The probe was prepared in that 12 μg. of plasmid which contains the human urokinase cDNA was digested with Pst I. There thereby results a 1.1 Kb part fragment of the cDNA which was subjected to electrophoresis (yield about 2 μg.).

The labelling of the partial fragment takes place analogously to Example 14. The pre-hybridization and hybridization of the filter takes place analogously to Example 19. The further detection steps take place analogously to Example 21.

It was shown that the filters of the plates which only contained urokinase recombinant phages give a positive signal for all plaques which were also readily visible in the second impression. In the case of the mixture, only as many positive signals as recombinant phages which had been added were seen. The lambda phages with other inserts gave no positive signal.

EXAMPLE 27

Northern Blot Hybridization (Detection of Actin-mRNA From Yeast)

The system according to the invention is also suitable for the sensitive and specific detection of RNA in Northern blots. In order to demonstrate thus, actin mRNA was detected in whole yeast RNA *Saccharomyces cerevisiae*. The actin gene (PNAS 77 (1980), 3912–3916) consists of two exons and one intron. In transcription, there first arises precursor mRNA (1679 bases). After capping, splicing and polyadenylation (carried out as in Meth. in Enzymol. 65 (1980) 380–391 and PNAS USA 77 (1980) 5201–5205) there results matured mRNA with a length of about 1400 bases (1370 bases+PolyA). Transfer to nitrocellulose as described in T. Maniatis et al., "Molecular Cloning", Cold Spring Harbor Laboratory, Cold Spring Harbor, N.Y. (1982) follows. The pre- and main hybridization and detection (18 hours) takes place as described in Example 19. For the detection, a digoxigenin-labelled actin-specific probe was used which consisted of a 2.3 kB actin Eco RI/Hind III fragment of the actin gene.

EXAMPLE 28

Detection of hepatitis B virus (HBV) in human sera by slot-blot analysis

The heptatitis B virus has an approximately 32 kb sized circular genome which is made up of two linear complementary strands. The 3'-end of one of the strands is variable. The 5'-ends of the two complementary strands are displaced with regard to one another. For detection of HBV via its DNA, a digoxigenin-labelled 1.8 kb Bam HI fragment (preparation according to Example 14) was used as probe which contains the double-stranded region for the core antigen, as well as parts of the DNA coding for the Prae-S1, Prae-S2 and X antigen (position 1.4–3.2 kb). Parallel to the digoxigenin detection were used biotin-(cf. Example 24) and $^{32}$P-labelled probes (labelling analogous to the working instructions of the BRL kit, cf. Example 24).

The investigated human sera are classified as positive or negative on the basis of the immunological labels HB$_s$Ag, HB$_c$Ag, anti-HB$_s$ and anti-HB$_c$.

Serum preparation:

For a double determination, 100 μl. centrifuged serum are mixed with 300 μl. 0.5M NaOH. After 5 minutes incubation at room temperature, it is again centrifuged for 5 min. In each case, 200 μl. of the supernatant are pipetted into a comb slot of the Minifolt ® apparatus and a vacuum then applied.

Preparation of the nylon filter:

Biodyne nylon membrane (1.2 μm. pore size) (Pall Bio Support Div. Glen Cove, N.Y.) is cut up to chamber size and prepared as follows:

placed for 5 min. in distilled water
15 min. in 10×SSC
dried for 5 min. under a heating lamp on Whatman ® paper.
Laying on 10×SSC-impregnated Whatman ® paper and
placing in the Minifold ® apparatus.

The probe collection plate is then laid on the filter, securely clamped and subsequently the sera are spotted on.

Further treatment of the filter:

The filters are taken from the Minifold ® apparatus and placed for, in each case, 5 min. on 10×SSC, 5×SSC and 1×SSC. One subsequently dries under a heating lamp and bakes for 2 hours at 80° C. in a vacuum.

Pre-hybridization and hybridization takes place analogously to Example 19.

The preparation of the radio-active probe takes place as described in the working instructions of the Sp6/T7 transcription kit of BOEHRINGER MANNHEIM GMBH, order No. 999644.

Pre-hybridization, hybridization, washing and development for the $^{32}$P probe take place as described in Maniatis (supra).

It is shown that with the process according to the invention, signals in the slot blot are only obtained with the positive but not with the negative sera. The control reactions with immunised serum are also negative. The comparison with corresponding radio-active detection shows analogous specificity. In contradistinction thereto, in the biotin system, distinctly higher background is to be seen.

HPV detection with the process according to the invention is very sensitive. In a dilution series, HPV sequences can be detected down to a serum dilution of $10^{-4}$ to $10^{-5}$. This corresponds to the sensitivity in the radio-active system. In the non-radio-active system, the corresponding negative sera do not give a signal at any dilution. In the biotin system, a distinct background is to be seen in the dilution series.

EXAMPLE 29

Digoxigenin-labelled dUTP is used in the polymerase chain reaction (PCR, analogous to EP-A 0200362) for the labelling of amplified DNA.

As sample is used: plasmid pBR 322 primer 1:
5'-GCTCCCTCGTGCGCTCTCCTGT-3' (SEQ ID NO:2)

primer 2:
5'-CCGCCTACATACCTCGCTCTGC-3' (SEQ ID NO: 3)

10 pg. sample, 300 ng. primer 1, 300 ng. primer 2, in each case 1 mmol/l. dATP, dCTP, dGTP, dTTP, 0.1 mmol/l. digoxigenin-dUTP in 67 mmol/l. Tris-HCl pH 8.8, 6.7 mmol/l. MgCl$_2$, 16.6 mmol/l. ammonium sulphate, 1 mmol/l. mercaptoethanol and 0.17 mg./ml. bovine serum albumin are denatured for 2 min. at 95° C. and hybridised for 3 min. at 40° C. Thereafter, 6 U

*Thermus aquaticus* DNA polymerase are added thereto and incubated for 3 min. at 65° C. (polymerisation). (The volume of the reaction amounts to 50 microlitres, the statements of concentration refer to this reaction volume). In all, 25 cycles (denaturing, hybridisation, polymerisation) were carried out.

Subsequently, in each case, 1/5 of the reaction batches were separated in 0.8% agarose gel and transferred according to the method of Southern (J. Mol. Biol. 98 (1975) 503) to nylon membranes (e.g. Hybond-N, Amersham). Alternatively, dilutions of 1:10 to $1:10^5$ were dropped on to nylon membranes and fixed. Blocking of the filters, conjugation reactions and colouring are carried out analogously to Example 21.

---

We claim:
1. Method for detection of a first nucleic acid sequence comprising contacting said sequence with a complementary nucleic acid probe under conditions favoring hybridization between said sequence and said probe, wherein said probe is a second nucleic acid sequence having bound thereto at least one steroid hapten selected from the group consisting of digoxin and digoxigenin, said steroid hapten being bound to said second nucleic acid sequence via a bridge of at least 4 atoms length at a position thereon which does not participate in formation of hydrogen bonds with said first sequence, contacting hybridized probe with a labelled antibody which specifically binds to said steroid hapten, and detecting said labelled antibody to detect said first nucleic acid sequence.

2. Method of claim 1 wherein said bridge is from 4 to 32 atoms in length.

3. Method of claim 1 wherein said bridge is from 11 to 16 atoms in length.

4. Method of claim 1 wherein said bridge contains hydrophilic groups.

5. Method of claim 1 wherein said bridge is linear.

6. Method of claim 1 wherein said bridge is branched and contains a hapten molecule at at least one chain end.

7. Method of claim 1 wherein said steroid hapten is bound to a nucleotide base via said bridge.

8. Method of claim 7 wherein said base is uracil or cytosine and said steroid hapten is bound to C5 via said bridge.

9. Method of claim 7 wherein said base is adenine or quanine and said steroid hapten is bound to C8 via said bridge.

10. Method of claim 1 wherein said steroid hapten is bound to a ribose via said bridge.

11. Method of claim 10 wherein said steroid hapten is bound to the 2' position of ribose via said bridge.

12. Method of claim 1 wherein said steroid hapten is bound to said bridge via an ester, amide, or ether bond.

13. Method of claim 1 wherein said antibody is labelled with an enzyme label, a radioactive label, a fluorescence label or a bioluminescent label.

14. Method of claim 13 wherein said antibody is labelled with an enzyme.

15. Method of claim 14 wherein said enzyme is alkaline phosphatase, peroxidase or beta galactosidase.

16. Method of claim 13 comprising detecting said labelled antibody via a redox reaction system.

17. Method of claim 16 wherein said enzyme is alkaline phosphatase and said redox reaction system comprises X phosphate and nitroblue tetrazolium.

18. Method of claim 13 comprising detecting said labelled antibody via a system using a leuko indicator.

19. Method of claim 13 comprising detecting said label with an indigoid compound and a tetrazolium salt.

20. Method of claim 1 wherein said first nucleic acid sequence is in a cell sample fixed to a solid support.

21. Method of claim 1 wherein said first nucleic acid sequence is in a smear of tissue sample.

22. Method of claim 1, wherein said hapten has been incorporated into said probe enzymatically.

23. Method of claim 22, wherein said hapten is bound to a deoxy or ribonucleoside triphosphate moiety and said moiety has been incorporated into said probe enzymatically via an enzyme selected from the group consisting of a DNA polymerase, an RNA polymerase, a reverse transcriptase and a terminal transferase.

24. Method of claim 1, wherein said hapten has been incorporated into said probe photochemically.

25. Method of claim 24, wherein said hapten is incorporated in the form of a photo-hapten.

26. Method of claim 1, wherein said hapten has been incorporated into said probe chemically.

27. Method of claim 26, wherein said hapten has been incorporated into said probe by incorporating a modified nucleoside phosphoamidite having a substitutable amino functional group into said probe as a protective group, removing said protective group, activating an ester, amide, or ether group of said hapten and reacting the activated hapten with said nucleoside phosphoamidite.

28. Method for detection of a first nucleic acid sequence comprising:
(a) contacting said first nucleic acid with at least two oligonucleotide primers under conditions favoring hybridization between said first nucleic acid sequence and said primers, wherein the first primer comprises a first nucleotide sequence which is complementary to a part of a nucleic acid sequence of a DNA strand to be detected and wherein the second primer comprises a different second nucleotide sequence which is identical to a part of a nucleotide sequence of said DNA strand to be detected,
(b) treating said mixture from (a) with a polymerase and deoxyribonucleotides under conditions favoring nucleic acid polymerization and in the presence of at least one deoxyribonucleotide having bound thereto at least one steroid hapten selected from the group consisting of digoxin and digoxigenin, said steroid hapten being bound to said deoxyribonucleotide via a bridge of at least 4 atoms length at a position thereon which does not participate in formation of hydrogen bonds with any other nucleotide,
(c) subjecting said mixture of (b) at least once to a cycle of denaturing, hybridizing and polymerizing according to steps (a) and (b),
(d) contacting said mixture from (c) with a labelled antibody which specifically binds to said steroid hapten, and
(e) detecting said labelled antibody as a detection of said first nucleic acid sequence.

29. Method of claim 28 wherein said polymerase is a *Thermus aquaticus* DNA polymerase.

30. Method of claim 28, wherein at least one of said primers is immobilized on a solid phase.

31. Method for detection of a first nucleic acid sequence comprising:
(a) contacting said first nucleic acid with at least two oligonucleotide primers under conditions favoring hybridization between said first nucleic acid sequence and said primers, wherein the first primer comprises a first nucleotide sequence which is complementary to a part of a nucleic acid sequence to be detected and wherein the second primer comprises a different second nucleotide sequence which is identical to a part of said nucleotide sequence to be detected,
(b) treating said mixture from (a) with a polymerase and deoxyribonucleotides under conditions favoring nucleic acid polymerization,
(c) subjecting said mixture of (b) at least once to a cycle of denaturing, hybridizing and polymerizing according to steps (a) and (b),
(d) repeating the cycle according to step (c) in the presence of at least one deoxyribonucleotide having bound thereto at least one steroid hapten selected from the group consisting of digoxin and digoxigenin, said steroid hapten being bound to said deoxyribonucleotide via a bridge of at least 4 atoms length at a position thereon which does not participate in formation of hydrogen bonds with any other nucleotide,
(e) contacting said mixture from (c) with a labelled antibody which specifically binds to said steroid hapten, and (f) detecting said labelled antibody as a detection of said first nucleic acid sequence.

32. Method of claim 31 wherein said polymerase is a Thermus aquaticus DNA polymerase.

33. Method of claim 31, wherein at least one of said primers is immobilized on a solid phase.

34. A deoxyribonucleotide or ribonucleotide having bound thereto at least one steroid hapten selected from the group consisting of digoxin and digoxigenin, said steroid hapten being bound to said deoxyribonucleotide or ribonucleotide via a bridge of at least 4 atoms length at a position which does not participate in formation of hydrogen bonds with any other nucleotide.

35. A deoxyribonucleotide or ribonucleotide triphosphate having bound thereto at least one steroid hapten selected from the group consisting of digoxin and digoxigenin, said steroid hapten being bound to said deoxyribonucleotide or ribonucleotide via a bridge of at least 4 atoms length at a position which does not participate in formation of hydrogen bonds with any other nucleotide.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 3104 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GAATACAAGC TTGCATGCCT GCAGGTCGAC TCTAGAGGAT CCCCGGGTAC CGAGCTCGAA      60
TTCCGGTCTC CCTATAGTGA GTCGTATTAA TTTCGATAAG CCAGCTGGGC CTCGCGCGTT     120
TCGGTGATGA CGGTGAAAAC CTCTGACACA TGCAGCTCCC GGAGACGGTC ACAGCTTGTC     180
TGTAAGCGGA TGCCGGGAGC AGACAAGCCC GTCAGGGCGC GTCAGCGGGT GTTGGCGGGT     240
GTCGGGGCGC AGCCATGACC CAGTCACGTA GCGATAGCGG AGTGTATATA CTGGCTTAAC     300
TATGCGGCAT CAGAGCAGAT TGTACTGAGA GTGCACCATA TGCGGTGTGA AATACCGCAC     360
AGATGCGTAA GGAGAAAATA CCGCATCAGG CGCTCTTCCG CTTCCTCGCT CACTGACTCG     420
CTGCGCTCGG TCGTTCGGCT GCGGCGAGCG GTATCAGCTC ACTCAAAGGC GGTAATACGG     480
TTATCCACAG AATCAGGGGA TAACGCAGGA AAGAACATGT GAGCAAAAGG CCAGCAAAAG     540
GCCAGGAACC GTAAAAAGGC CGCGTTGCTG GCGTTTTTCC ATAGGCTCCG CCCCCCTGAC     600
GAGCATCACA AAAATCGACG CTCAAGTCAG AGGTGGCGAA ACCCGACAGG ACTATAAAGA     660
TACCAGGCGT TTCCCCCTGG AAGCTCCCTC GTGCGCTCTC CTGTTCCGAC CCTGCCGCTT     720
ACCGGATACC TGTCCGCCTT TCTCCCTTCG GGAAGCGTGG CGCTTTCTCA ATGCTCACGC     780
TGTAGGTATC TCAGTTCGGT GTAGGTCGTT CGCTCCAAGC TGGGCTGTGT GCACGAACCC     840
CCCGTTCAGC CCGACCGCTG CGCCTTATCC GGTAACTATC GTCTTGAGTC CAACCCGGTA     900
AGACACGACT TATCGCCACT GGCAGCAGCC ACTGGTAACA GGATTAGCAG AGCGAGGTAT     960
GTAGGCGGTG CTACAGAGTT CTTGAAGTGG TGGCCTAACT ACGGCTACAC TAGAAGGACA    1020
GTATTTGGTA TCTGCGCTCT GCTGAAGCCA GTTACCTTCG GAAAAAGAGT TGGTAGCTCT    1080
TGATCCGGCA AACAAACCAC CGCTGGTAGC GGTGGTTTTT TTGTTTGCAA GCAGCAGATT    1140
ACGCGCAGAA AAAAGGATC TCAAGAAGAT CCTTTGATCT TTTCTACGGG GTCTGACGCT    1200
CAGTGGAACG AAAACTCACG TTAAGGGATT TTGGTCATGA GATTATCAAA AAGGATCTTC    1260
ACCTAGATCC TTTTAAATTA AAAATGAAGT TTTAAATCAA TCTAAAGTAT ATATGAGTAA    1320
ACTTGGTCTG ACAGTTACCA ATGCTTAATC AGTGAGGCAC CTATCTCAGC GATCTGTCTA    1380
TTTCGTTCAT CCATAGTTGC CTGACTCCCC GTCGTGTAGA TAACTACGAT ACGGGAGGGC    1440
TTACCATCTG GCCCCAGTGC TGCAATGATA CCGCGAGACC CACGCTCACC GGCTCCAGAT    1500
TTATCAGCAA TAAACCAGCC AGCCGGAAGG GCCGAGCGCA GAAGTGGTCC TGCAACTTTA    1560
TCCGCCTCCA TCCAGTCTAT TAATTGTTGC CGGGAAGCTA GAGTAAGTAG TTCGCCAGTT    1620
```

-continued

| | | | | | | |
|---|---|---|---|---|---|---|
| AATAGTTTGC | GCAACGTTGT | TGCCATTGCT | ACAGGCATCG | TGGTGTCACG | CTCGTCGTTT | 1680 |
| GGTATGGCTT | CATTCAGCTC | CGGTTCCCAA | CGATCAAGGC | GAGTTACATG | ATCCCCCATG | 1740 |
| TTGTGCAAAA | AAGCGGTTAG | CTCCTTCGGT | CCTCCGATCG | TTGTCAGAAG | TAAGTTGGCC | 1800 |
| GCAGTGTTAT | CACTCATGGT | TATGGCAGCA | CTGCATAATT | CTCTTACTGT | CATGCCATCC | 1860 |
| GTAAGATGCT | TTTCTGTGAC | TGGTGAGTAC | TCAACCAAGT | CATTCTGAGA | ATAGTGTATG | 1920 |
| CGGCGACCGA | GTTGCTCTTG | CCCGGCGTCA | ATACGGGATA | ATACCGCGCC | ACATAGCAGA | 1980 |
| ACTTTAAAAG | TGCTCATCAT | TGGAAAACGT | TCTTCGGGGC | GAAAACTCTC | AAGGATCTTA | 2040 |
| CCGCTGTTGA | GATCCAGTTC | GATGTAACCC | ACTCGTGCAC | CCAACTGATC | TTCAGCATCT | 2100 |
| TTTACTTTCA | CCAGCGTTTC | TGGGTGAGCA | AAAACAGGAA | GGCAAAATGC | CGCAAAAAG | 2160 |
| GGAATAAGGG | CGACACGGAA | ATGTTGAATA | CTCATACTCT | TCCTTTTTCA | ATATTATTGA | 2220 |
| AGCATTTATC | AGGGTTATTG | TCTCATGAGC | GGATACATAT | TTGAATGTAT | TTAGAAAAAT | 2280 |
| AAACAAATAG | GGGTTCCGCG | CACATTTCCC | CGAAAAGTGC | CACCTGACGT | CTAAGAAACC | 2340 |
| ATTATTATCA | TGACATTAAC | CTATAAAAAT | AGGCGTATCA | CGAGGCCCTT | TCGTCTCGCG | 2400 |
| CGTTTCGGTG | ATGACGGTGA | AAACCTCTGA | CACATGCAGC | TCCCGGAGAC | GGTCACAGCT | 2460 |
| TGTCTGTAAG | CGGATGCCGG | GAGCAGACAA | GCCCGTCAGG | GCGCGTCAGC | GGGTGTTGGC | 2520 |
| GGGTGTCGGG | GCTGGCTTAA | CTATGCGGCA | TCAGAGCAGA | TTGTACTGAG | AGTGCACCAT | 2580 |
| ATCGACGCTC | TCCCTTATGC | GACTCCTGCA | TTAGGAAGCA | GCCCAGTAGT | AGGTTGAGGC | 2640 |
| CGTTGAGCAC | CGCCGCCGCA | AGGAATGGTG | CATGCAAGGA | GATGGCGCCC | AACAGTCCCC | 2700 |
| CGGCCACGGG | CCTGCCACCA | TACCCACGCC | GAAACAAGCG | CTCATGAGCC | CGAAGTGGCG | 2760 |
| AGCCCGATCT | TCCCCATCGG | TGATGTCGGC | GATATAGGCG | CCAGCAACCG | CACCTGTGGC | 2820 |
| GCCGGTGATG | CCGGCCACGA | TGCGTCCGGC | GTAGAGGATC | TGGCTAGCGA | TGACCCTGCT | 2880 |
| GATTGGTTCG | CTGACCATTT | CCGGGTGCGG | GACGGCGTTA | CCAGAAACTC | AGAAGGTTCG | 2940 |
| TCCAACCAAA | CCGACTCTGA | CGGCAGTTTA | CGAGAGAGAT | GATAGGGTCT | GCTTCAGTAA | 3000 |
| GCCAGATGCT | ACACAATTAG | GCTTGTACAT | ATTGTCGTTA | GAACGCGGCT | ACAATTAATA | 3060 |
| CATAACCTTA | TGTATCATAC | ACATACGATT | TAGGTGACAC | TATA | | 3104 |

(2) INFORMATION FOR SEQ ID NO: 2:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 2:

GCTCCCTCGT GCGCTCTCCT GT (2) INFORMATION FOR SEQ ID NO: 3:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 3:

CCGCCTACAT ACCTCGCTCT GC